United States Patent
Graudejus et al.

(10) Patent No.: US 12,343,544 B2
(45) Date of Patent: Jul. 1, 2025

(54) PERIPHERAL NERVE INTERFACE DEVICE

(71) Applicant: BMSEED LLC, Phoenix, AZ (US)

(72) Inventors: Oliver Graudejus, Tempe, AZ (US); Cami C. Rowan, Tempe, AZ (US); Timothy M. Otchy, Brooklyn, NY (US)

(73) Assignee: BMSEED LLC, Mesa, AZ (US)

( * ) Notice: Subject to any disclaimer, the term of this patent is extended or adjusted under 35 U.S.C. 154(b) by 487 days.

(21) Appl. No.: 17/840,275

(22) Filed: Jun. 14, 2022

(65) Prior Publication Data

US 2022/0401746 A1    Dec. 22, 2022

Related U.S. Application Data

(60) Provisional application No. 63/211,735, filed on Jun. 17, 2021.

(51) Int. Cl.
| | | |
|---|---|---|
| *A61N 1/05* | (2006.01) | |
| *A61N 1/36* | (2006.01) | |
| *A61N 1/372* | (2006.01) | |

(52) U.S. Cl.
CPC ....... *A61N 1/37205* (2013.01); *A61N 1/0556* (2013.01); *A61N 1/36053* (2013.01)

(58) Field of Classification Search
None
See application file for complete search history.

(56) References Cited

U.S. PATENT DOCUMENTS

| | | | |
|---|---|---|---|
| 6,587,725 B1 * | 7/2003 | Durand | A61N 1/3601 607/42 |
| 7,491,892 B2 * | 2/2009 | Wagner | H05K 1/11 174/254 |

(Continued)

FOREIGN PATENT DOCUMENTS

WO    WO-2018022838 A1 *    2/2018    ........... A61N 1/0556

OTHER PUBLICATIONS

Cho et al., "Advanced Neural Interface toward Bioelectronic Medicine Enabled by Micro-Patterned Shape Memory Polymer," Micromachines, 2021, vol. 12, 720, 9 pages.

(Continued)

*Primary Examiner* — Erica S Lee
(74) *Attorney, Agent, or Firm* — Birch, Stewart, Kolasch & Birch, LLP

(57) ABSTRACT

A peripheral nerve interface including a microclip having a substantial U-shape and including an upper entry portion for entry of a nerve into the microclip and a lower seating portion for seating the nerve in the lower seating portion of the microclip; a stretchable microelectrode array including a plurality of electrodes, wherein the stretchable microelectrode array has a proximal end portion fixed to the microclip and a portion that is moveable and dragged into the upper entry portion and then the lower entry portion of the microclip in response to the microclip be positioned on the nerve; and an interface connected to a distal end of the stretchable microelectrode array and configured to interface with an external device for applying electrical stimulation to the nerve seated in the lower seating portion and for recording electrical characteristic of the nerve seated in the lower seating portion via the plurality of electrodes in the stretchable microelectrode array.

17 Claims, 19 Drawing Sheets
(19 of 19 Drawing Sheet(s) Filed in Color)

(56) References Cited

U.S. PATENT DOCUMENTS

2020/0316373 A1* 10/2020 Bolea .................. A61N 1/0556
2021/0290949 A1* 9/2021 Holinski ................ B33Y 80/00

OTHER PUBLICATIONS

Decataldo et al., "Stretchable low impedance electrodes for bioelectronic recording from small peripheral nerves," Scientific Reports, 2019, vol. 9:10598, 9 pages.

Foldes et al., "Design, fabrication and evaluation of a conforming circumpolar peripheral nerve cuff electrode for acute experimental use," Journal of Neuroscience Methods, 2011, vol. 196(1), 14 pages.

González-González et al., "Thin film multi-electrode softening cuffs for selective neuromodulation," Scientific Reports, 2018, vol. 8:16390, 15 pages.

Graudejus et al., "A soft and stretchable bilayer electrode array with independent functional layers for the next generation of brain machine interfaces," Journal of Neural Engineering, 2020, vol. 17(5):056023, 22 pages.

Lancashire et al., "Microchannel neural interface manufacture by stacking silicone and metal foil laminae," Journal of Neural Engineering, 2016, vol. 13, 034001, 9 pages.

Lienemann et al., "Stretchable gold nanowire-based cuff electrodes for low-voltage peripheral nerve stimulation," Journal of Neural Engineering, 2021, vol. 18, 045007, 11 pages.

Otchy et al., "Printable microscale interfaces for long-term peripheral nerve mapping and precision control," Nature Communications, 2020, vol. 11:4191, 16 pages.

Pearre et al., "Fast micron-scale 3D printing with a resonant-scanning two-photon microscope," Additive Manufacturing, 2019, vol. 30, 100887, 10 pages.

Song et al., "Adaptive self-healing electronic epineurium for chronic bidirectional neural interfaces," Nature Communications, 2020, vol. 11:4195, 10 pages.

Tyler et al., "Functionally selective peripheral nerve stimulation with a flat interface nerve electrode," IEEE Transactions on Neural Systems and Rehabilitation Engineering, vol. 10, No. 4, 2002, pp. 294-303.

Yu et al., "A parylene self-locking cuff electrode for peripheral nerve stimulation and recording," Journal of Microelectromechanical Systems, vol. 23, No. 5, 2014, pp. 1025-1035.

* cited by examiner (a)

(b)

PERIPHERAL NERVE INTERFACE DEVICE

CROSS REFERENCE TO RELATED APPLICATIONS

This non-provisional application claims the benefit under 35 U.S.C. § 119(e) to U.S. Provisional Application No. 63/211,735, filed on Jun. 17, 2021, which is incorporated by reference into the present application.

This invention was made with government support under Contract No. NS111685 awarded by the National Institute of Health. The government has certain rights in the invention.

COLOR DRAWINGS

The patent or application file contains at least one color drawing. Copies of this patent or patent application publication with color drawings will be provided by the USPTO upon request and payment of the necessary fee.

BACKGROUND OF THE INVENTION

Field of the Invention

A peripheral nerve interface device including a soft and stretchable microelectrode array for circumferential bioelectronic interfacing with nerves.

Description of the Related Art

Implantable neural interfaces are used to study and treat the nervous system. For example, cochlear implants restore hearing in deaf children, deep brain stimulation alleviates Parkinsonian symptoms, and spinal cord neuromodulation attenuates neuropathic pain. A broad range of diseases can thus be treatable through precise intervention in the peripheral nervous system (PNS). The hope for such bioelectronic therapeutics has prompted the development of devices targeting a variety of nerves and ganglia throughout the PNS. However, persistent challenges bridging the mismatch in mechanical properties and scale have hindered the realization of peripheral nerve interfaces (PNIs) mediating long-lasting interfacing with smaller sized nerves. In addition, related art interfaces only record activity on one small side surface of the nerve.

Further, recording and stimulating peripheral nerves is an area of increasing research interest and clinical importance, especially for restoring control of paralyzed muscles, dexterous command of advanced bionic limbs, and the therapeutic modulation of signaling in the PNS to alleviate pathological inflammation, pain, and other chronic disorders. FDA approved clinical applications of PNIs are largely limited to Vagus Nerve Stimulation (VNS) and Sacral Nerve Stimulation (SNS). The vagus nerve and the sacral nerve are both large diameter nerves (up to 4.8 and 1.4 mm, respectively) carrying thousands of individual nerve fibers, and thus the potential for unintended off-target neuromodulatory effects is high.

In addition, peripheral nerves carry sensory (afferent) and motor (efferent) signals between the central nervous system and other parts of the body. In more detail, peripheral nerves are heterogeneous viscoelastic structures, with elastic and shear moduli in the 5-500 kPa range, that exist in a biomechanically dynamic environment, and accommodate body movement and local tissue strain through a combination of deformation and displacement. However, related art PNIs have a high elastic moduli in the gigapascal range, and are thus rigid compared to body tissues. Thus, related art PNIs fail to accommodate the biomechanical properties of host tissues and cannot maintain stable recording and stimulation characteristics over time.

Related art PNI technologies include cuff electrodes that envelop the nerve, sieve electrodes that provide mechanical guidance for regenerating nerves, and stiff penetrating electrodes designed to be inserted longitudinally or transverse to the direction of the fibers. However, the related art devices do not sufficiently address the biomechanical and environmental challenges required for long term reliable stimulation and recording.

Moreover, related art PNI technologies have a significant tradeoff between invasiveness, which leads to nerve damage, and selectivity/sensitivity for achieving a result of close proximity to the nerve fibers. For example, cuff electrodes are the least invasive, but are stiff and bulky compared to body tissues and suffer from limited selectivity for stimulation and a lack of recording sensitivity due to poor mechanical compliance with the nerve tissue and a comparatively large distance from the nerve fibers. Sieve electrodes are the most invasive because require the nerve to be cut and regenerated through the sieve, with an unavoidable transient damage phase and low probability of a recording site being close to the regrown nerve fibers. In addition, designs with penetrating probes do not demonstrate long-term stability, have shown substantial scar-tissue deposition within the nerve, and are prone to cause trauma in the nerve during implant.

The Utah Slanted Electrode Array (USEA), for example, comprises a high-density array of silicon shanks (Young's modulus>100 GPa) that penetrate the nerve to interface closely with the nerve fibers. However, the USEA exhibits a large mismatch in mechanical properties with the nerve which causes significant and irrecoverable nerve damage as well as scar tissue formation around the electrodes, limiting their effectiveness and usable lifetime.

SUMMARY OF THE INVENTION

Accordingly, one object of the present invention is to address the above-noted and other problems of the related art.

Another object of the present invention is to provide a novel PNI that can chronically attach to small distal branches of the vagus and sacral nerves, for example, with diameters less than 200 µm, establish high-resolution recording and stimulation for precise targeting and modulation of signals within the terminal branches of the PNS, and elicit desired modulatory effects without altering nerve health or other functionalities.

Still another object of the present invention is to provide a chronically implantable PNI with high-biomechanical compliance with host tissues and that makes a high-quality bi-directional interface with a small nerve target.

Yet another object of the present invention is to provide a novel PNI integrating a 2-photon 3D printed microclip with a clamping mechanism for clamping a stretchable microelectrode array (sMEA) and with flexible hinges to accommodate a variation (e.g., 10% variation) in nerve diameter without damaging the nerve or sacrificing recording quality.

Another objective of the present invention is to provide a novel microclip PNI (µcPNI) for bio-electronically interfacing with small nerves.

Still another objective of the present invention is to provide a novel microclip PNI including an sMEA that wraps around a nerve to record discrete signals on the circumference of the nerve.

To achieve these and other advantages and in accordance with the purpose of the present invention, as embodied and broadly described herein, the present invention provides in one aspect a peripheral nerve interface including a microclip having a substantial U-shape and including an upper entry portion for entry of a nerve into the microclip and a lower seating portion for seating the nerve in the lower seating portion of the microclip; a stretchable microelectrode array including a plurality of electrodes, wherein the stretchable microelectrode array has a first end portion fixed to the microclip and a second end portion that is moveable and dragged into the upper entry portion and then the lower entry portion of the microclip in response to the microclip be positioned on the nerve; and an interface connected to the second end of the stretchable microelectrode array and configured to interface with an external device for applying electrical stimulation to the nerve seated in the lower seating portion and for recording electrical characteristic of the nerve seated in the lower seating portion via the plurality of electrodes in the stretchable microelectrode array.

In another aspect, the present invention provides a method of surgical attaching a microclip to a nerve in vivo, and a method of manufacturing a peripheral network interface for interfacing with a nerve in vivo.

Further scope of applicability of the present invention will become apparent from the detailed description given hereinafter. However, the detailed description and specific examples, while indicating preferred embodiments of the invention, are given by illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings, which are given by illustration only, and thus are not limitative of the present invention, and wherein.

DETAILED DESCRIPTION OF THE EMBODIMENTS

Reference will now be made in detail to the preferred embodiments of the present invention, examples of which are illustrated in the accompanying drawings.

Figure 1:
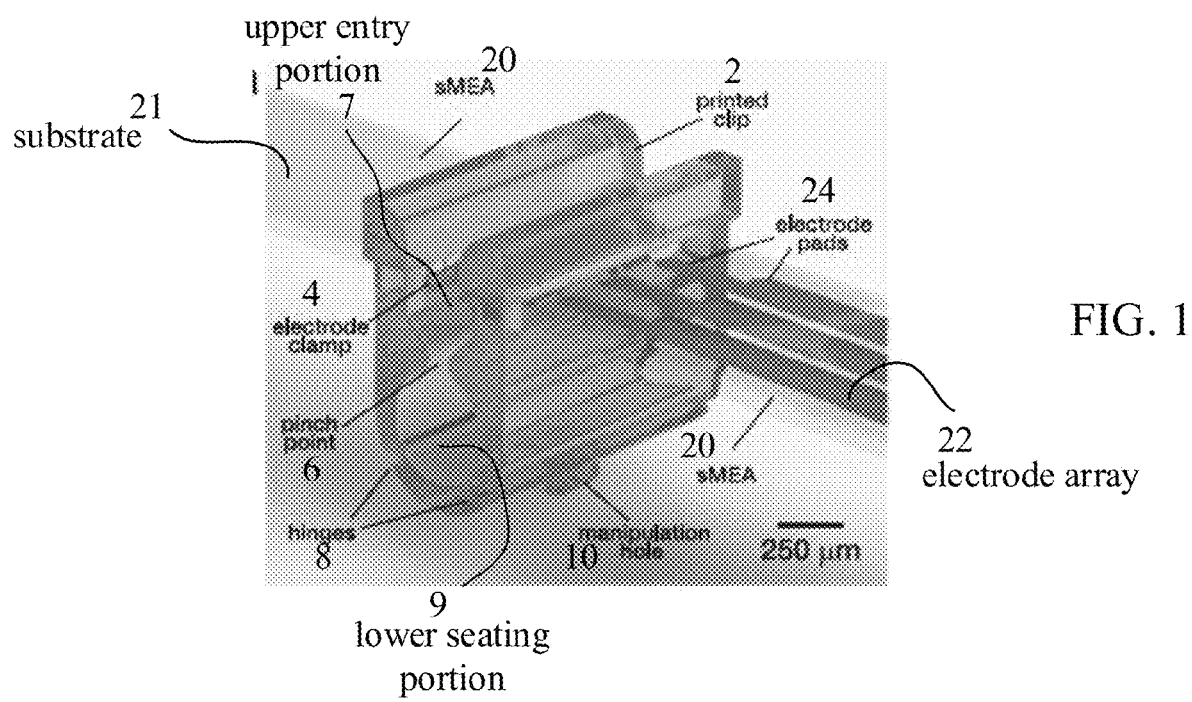
FIG. 1 is an overview illustrating a novel microclip PNI (μcPNI) according to an embodiment of the present invention.
Figure 2:
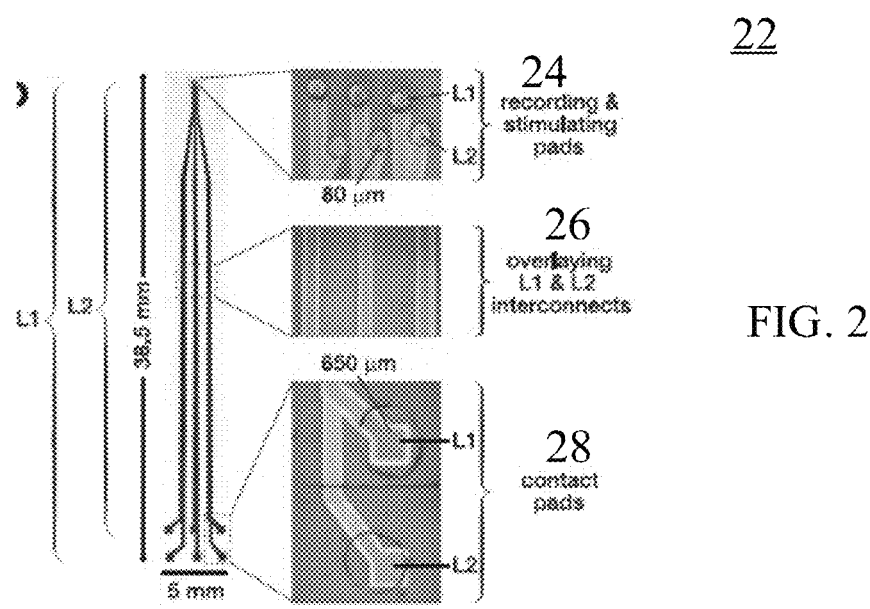
FIG. 2 is an overview illustrating an sMEA component of the μcPNI shown in FIG. 1 according to one embodiment of the present invention.
Figure 3:
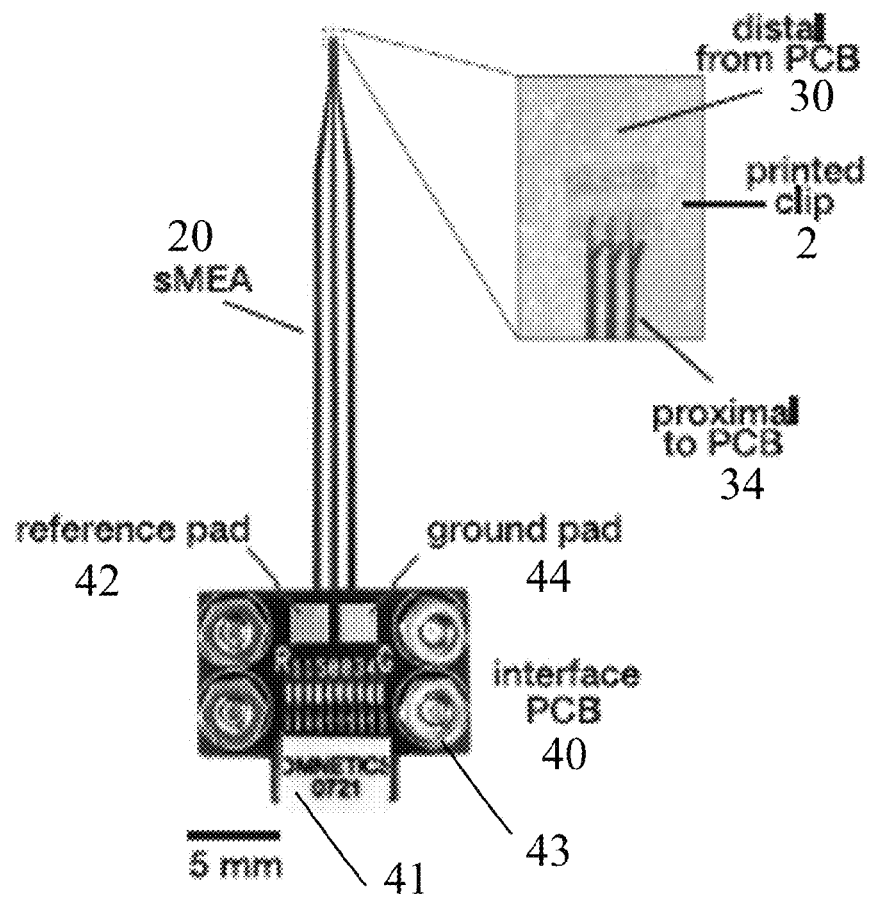
FIG. 3 includes overviews of an μcPNI according to an embodiment of the present invention.
Figure 3:
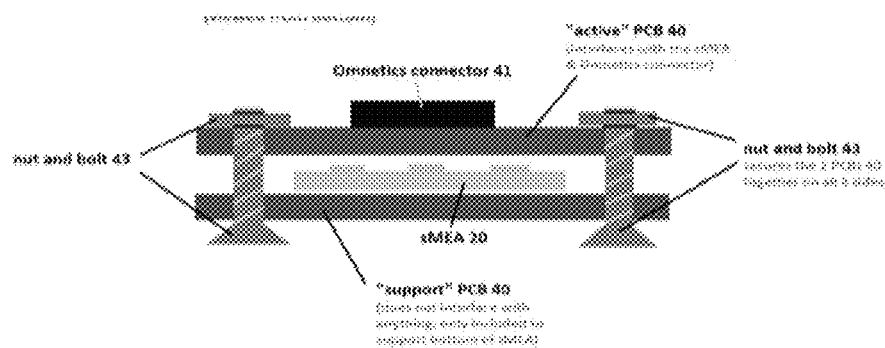

FIGS. 1-3 include overviews illustrating a novel μcPNI according to an embodiment of the present invention. As shown, the μcPNI includes a printed microclip 2 integrated with an sMEA 20. The sMEA 20 includes a soft and stretchable substrate 21 (e.g., elastomeric substrate) and a stretchable electrode array 22 embedded within the substrate 21. The electrode array 22 includes electrode pads 24 for recording electrical activity of the nerve, electrode interconnects 26 and contact pads 28 (see FIG. 2). In addition, as shown in FIG. 1, the distal part or end part of the sMEA 20 only includes the substrate 21 and does not contain electrodes or traces of the electrode array 22, and the proximal part or other end part of the sMEA 20 contains the electrode traces of the electrode array 22.

In one embodiment, the sMEA 20 is also compression bonded between Printed Circuit Boards (PCBs) 40, described later in FIG. 3. Further, the sMEA 20 is soft and stretchable and does not fail due to body-dynamics-induced bending strain and fatigue. The microclip 2 is also preferably manufactured using a 3D printed resonant Direct-Laser-Write (rDLW) technology that rapidly structures a biostable photoresist (IP-Dip) with approximately 1 μm minimum feature sizes. Other photoresists can also be used.

Figure 8:
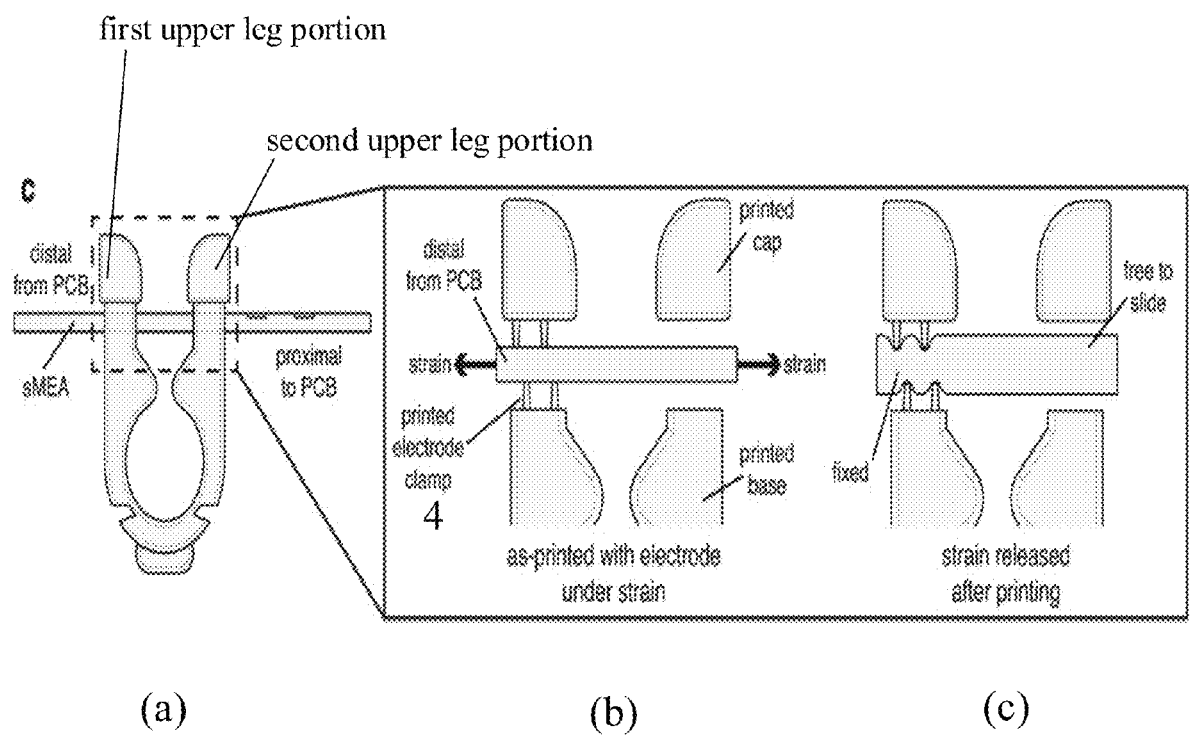
FIG. 8 is an overview illustrating a process of clamping the sMEA to the microclip according to an embodiment of the present invention.

As shown in FIG. 1, the printed microclip 2 includes an electrode clamp 4 for clamping one end (the distal end) of the sMEA 20, while the other end (the proximate end) of the sMEA 20 is advantageously unclamped so as to move freely within an opening of the microclip 2 (discussed in more detail in FIG. 8).

As shown, the microclip 2 has a substantial U-shape with a pinch point 6 separating the microclip 2 into a first upper entry portion 7 for entry of a nerve into the microclip 2, and a lower seating portion or cavity 9 for seating and retaining the nerve wrapped by electrodes of the electrode array 22 into the lower seating portion 9. The distance or width of the pinch point 6 can be increased by passing the nerve wrapped by electrodes of the electrode array 22 through the pinch point 6 by using the manipulation hole 10 (discussed in more detail in FIG. 4). In addition, the microclip 2 includes hinges 8 (e.g., flexion cut-out portions) that allow the microclip 2 to advantageously adjust to approximately 10% variations in nerve diameter. That is, the hinges 8 flex under μN-scale forces. Thus, the microclip 2 can accommodate both natural, subject-to-subject variation in anatomy and changes in nerve size due to post-implant inflammation/swelling, disease processes, and subject/nerve growth. The hinges 8 can also be made using through-holes, ring hinges, under-polymerizing the resist, etc.

That is, under force applied by the nerve wrapped in the sMEA 20 pressing against the pinch point 6, the 3D printed microclip 2 hinges open via the flex in the hinges 8, allowing the sMEA 20 to wrap snuggly around the nerve as it moves through the pinch point 6 and into the retention cavity or lower seating portion 9.

In addition, the flexible substrate 21 of the sMEA 20 in one embodiment comprises an elastomeric substrate or more specifically a polydimethylsiloxane (PDMS) substrate having a Young's Modulus of 2 MPa, which advantageously reduces a mismatch in biomechanical properties with the nerve tissue. The flexible substrate 21 can also be made of other elastomeric materials. Further, the 3D printed microclip 2 securely anchors the sMEA 20 on the nerve without needing sutures or adhesives, and allows for an arbitrary placement of the electrodes included in the electrode array 22 around a circumference of the nerve. Thus, discrete signals can be recorded around the circumference of the nerve, rather than on just one small side area of the nerve.

Next, FIG. 2 illustrates details of the electrode array 22. As shown in FIG. 2, the electrode array 22 includes an array of electrodes (six in the example in FIG. 2) having recording and stimulating pads 24, overlaying L1 (layer 1) and L2 (layer 2) interconnects 26, and contact pads 28. In this example, the six electrodes include three electrodes on layer 1 (L1) and three electrodes on layer 2 (L2). Further, as shown in FIG. 2, the recording and stimulating pads 24 are arranged to cover different portions of the nerve and thus cover a circumference of the nerve wrapped with the electrode array 22. Also, each contact pad 28 is connected to a corresponding recording and stimulating pad 24 via an interconnect 26. Six electrodes are illustrated as an example in FIG. 2, and more or less electrodes can be used.

Thus, in the embodiment in FIG. 2, there are six recording and stimulating pads 24, six interconnects 26 and six contact pads 28. Because the electrodes are formed or routed on different layers L1 and L2, it is possible to maximize the electrode density and reduce the overall dimensions of the device without compromising yield. In another embodiment, the electrodes can be formed and differently routed in a single layer or more than two layers. Further, the recording sites or pads 24 of the electrodes (e.g., 80 μm diameter) are connected via the electrode leads or interconnects 26 (e.g., width: 100-380 μm) to the contact pads 28 (e.g., width: 650 μm) of the PCB.

In addition to reducing the complexity of surgical manipulation, the wrap-on-implant allows for placing the electrodes recording and stimulating pads 24 of the electrode array 22 at arbitrary points on the circumference of the nerve 100 and eliminates the need for suturing or surgical adhesives to stabilize the preparation. Thus, the electrode pads 24 can be positioned around a circumference of the nerve such that discrete signals can be advantageously recorded on the circumference of the nerve.

Next, FIGS. 3(*a*) and (*b*) includes overviews of a fabricated μcPNI having an sMEA 20 sandwiched between PCBs 40. As shown, the PCBs 40 include an interface connector 41 (e.g., made by Omnetics) according to an embodiment of the present invention. A wireless chip or interface can also be used to connect to an external control device.

In addition, FIG. 3(*b*) is a side view of the PCBs 40 arranged to sandwich the sMEA 20 therebetween. In more detail, as shown in FIGS. 3(*a*) and (*b*), the PCBs 40 include a securing mechanism 43 (e.g., nuts and bolts) for securing the sandwiched PCBs 40. The μcPNI can then be connected to a controlling device via the interface connector 41. The controlling device applies electrical stimulation of the electrodes and/or records electrical characteristics of the nerve's response. The controlling device can record stimulation-evoked nerve activity as well as spontaneous nerve activity. An example of such a controlling device includes the Intan RHS 128ch recording/stimulation controller made by Intan Technologies. A wireless interface connector can also be used to communicate with the controlling device.

As shown, the interface PCBs 40 also include a reference pad 42 and a ground pad 44. The reference pad 42 is used to subtract a reference signal from the signal of each recording and stimulating electrode pads 24 on the sMEA 20 and the ground pad 44 provides a ground. Thus, as shown in FIG. 3(*a*), the sMEA 20 includes the recording and stimulating pads 24, overlaying interconnects 26 and contact pads 28. FIG. 3(*a*) illustrates the printed microclip 2 positioned at a distal end 30 of the PCBs 40. As shown in FIG. 3(*a*), the proximal end 34 of the microclip 2 is closer to the PCBs 40 than the distal end 30.

Thus, with reference to FIGS. 1-3, the printed microclip 2 combined and integrated with the sMEA 20 can be used to wrap a nerve in an electrode array, without damaging the nerve, so that the nerve can be advantageously electrically stimulated and/or electrical characteristics of the nerve can be recorded. In addition, the embodiment in FIGS. 1-3 includes a total of six electrodes for providing electrical stimulation and for recording electrical activity of the nerve. However, any number of electrodes may be used.

Further, each electrode can be independently controlled. Thus, electrical pulses of varying patterns can be selectively applied to the nerve. For example, a first electrode can be used to apply a first electrical pulse at a first time, the second electrode can be used to apply a second electrical pulse at a second time closely following the first electrical pulse. The magnitudes of each electrical pulse can also be individually set so the first electrical pulse has a magnitude twice the second electrical pulse, for example. Electrodes three to six can also be controlled to record electrical activity of the nerve before, during, and after the application of electrical stimulation.

The μcPNI can also be selectively controlled via the controller to perform the tasks described above including recording stimulation-evoked nerve activity and spontaneous nerve activity (e.g., using the Intan RHS 128ch recording/stimulation controller). The controller can be connected via the interface connector 41 on the interface PCB or active PCB 40. In addition, to facilitate the electrical connection to the external test equipment, the contact pads 28 (FIG. 2) on the sMEA 20 are preferably compression bonded to the PCBs 40, with silver paste applied to the contact pads 28 to ensure a low-impedance junction.

Figure 5:
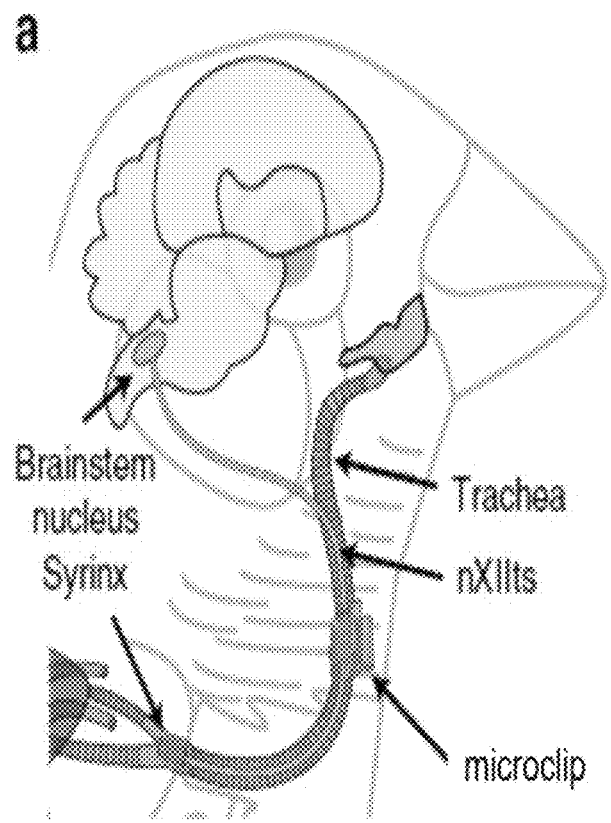
FIG. 5 includes an overview and a photomicrograph of an μcPNI implanted on a TSN of a zebra finch according to an embodiment of the present invention.
Figure 5:
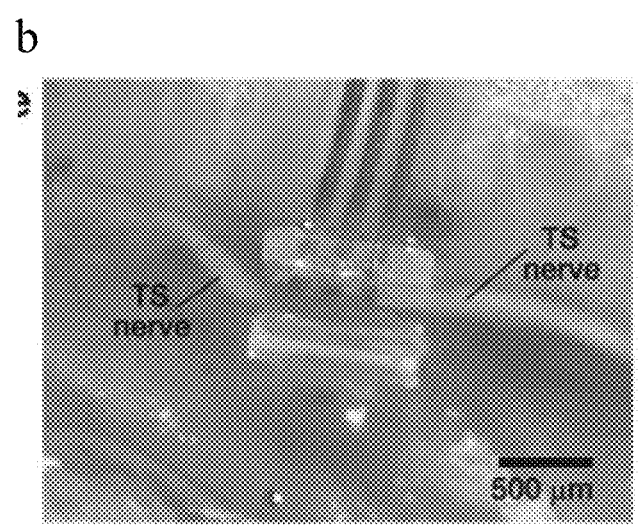
Figure 6:
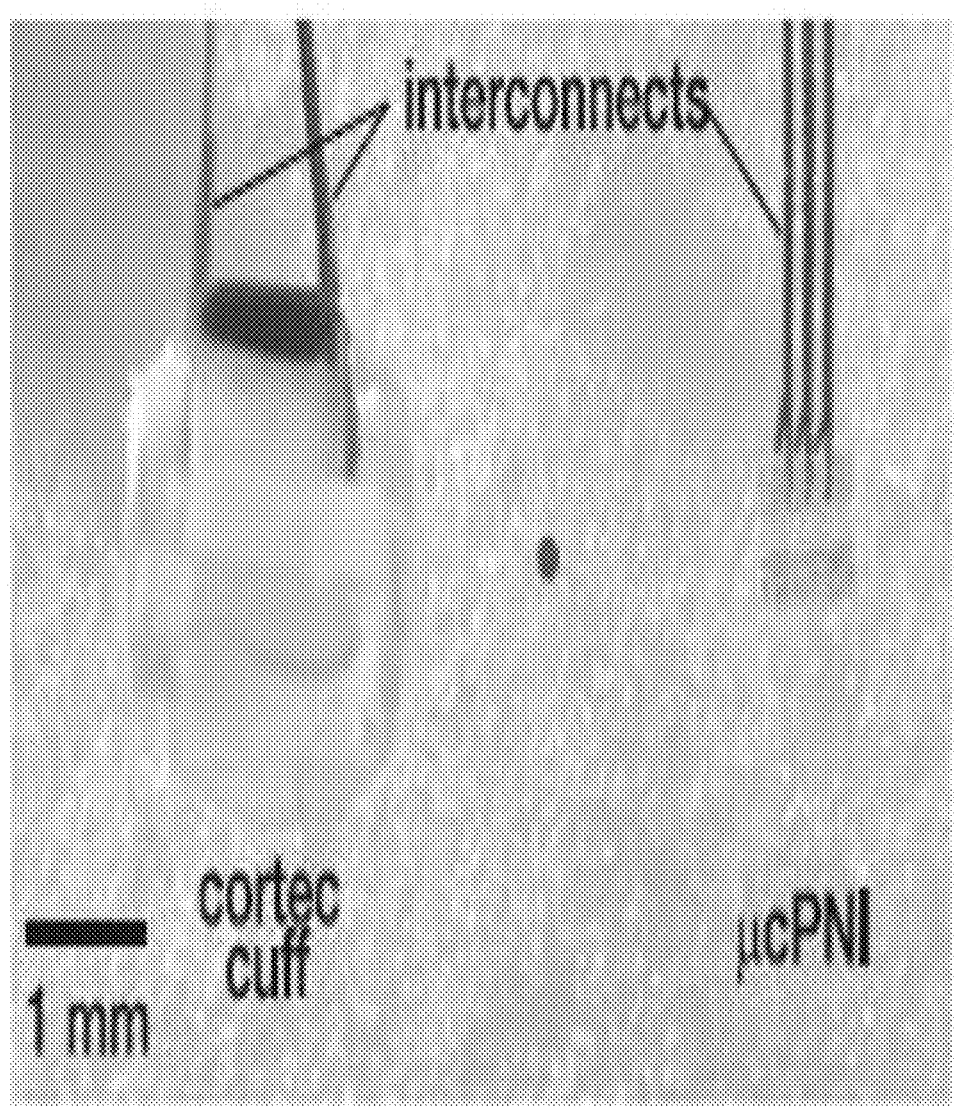
FIG. 6 is a photomicrograph comparing a 150 μm nerve diameter, for example, to an μcPNI and a Cortec silicone nerve cuff.

The printed microclip 2 enables significant miniaturization, keeping the overall scale of the μcPNI (800×500×800 μm) comparable to that of an implant target (e.g., the 150 μm diameter songbird TSN 100 in FIG. 5) and more than an order of magnitude smaller than a related art such as the Cortec cuff PNIs (see FIG. 6).

Figure 4:
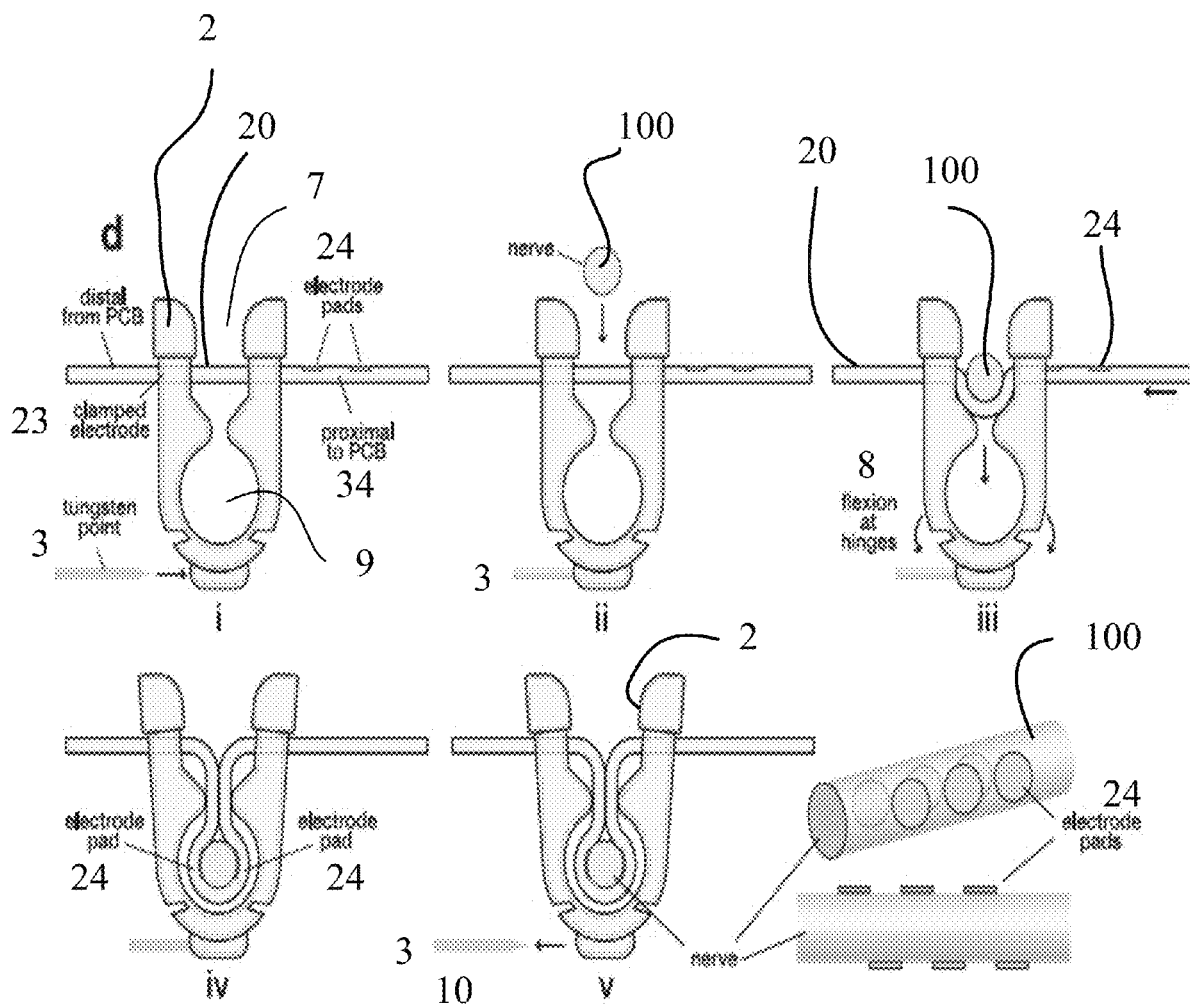
FIG. 4 is a schematic illustrating a nerve implantation process of the μcPNI according to an embodiment of the present invention.

Next, FIG. 4 is a schematic illustration of an implantation process of the μcPNI according to an embodiment of the present invention. As shown, the μcPNI can be implanted by inserting a sharpened tungsten point (tool) 3 in the manipulation hole 10 of the microclip 2 to advance the μcPNI towards the nerve 100 (FIGS. 4(*i*) and (*ii*)). In more detail, the point tool 3 (e.g., tungsten point) is inserted into the manipulation hole 10 and the microclip 2 can be moved toward the nerve using surgical forceps grasping the point tool 3, for example. Placing the manipulation hole 10 on the bottom portion of the microclip 2 also minimizes potential damage to the nerve (e.g., grabbing the clip directly could squeeze and damage the nerve).

Then, the nerve 100 contacts the sMEA 20 and drags the sMEA 20 wrapped around the nerve into the upper entry portion 7 of the microclip 2 (FIG. 4(*iii*)), and the sMEA 20 wraps around the nerve 100 as it enters the lower seating portion 9 of the microclip 2 (FIG. 4(*iv*)). The point tool 3 can then be retracted from the manipulation hole 10 (FIG. 4(*v*)). Further, the lower right corner of FIG. 4 includes isometric and top views of the nerve 100 and an example of the positions of the relative electrode pads 24 of the electrode array 22 after implant.

In more detail, FIG. 4(*i*) illustrates the fabricated μcPNI with the microclip 2 and sMEA 20. The distal end of the sMEA 20 is also pinched or clamped to the printed microclip 2, as described later in FIG. 8. The electrode recording and stimulating pads 24 are also disposed adjacent to the printed microclip 2, so the electrode pads 24 will advantageously be pulled to wrap around nerve 100 as the nerve 100 is moved into lower seating portion 9. That is, as shown in FIGS. 4(*ii*) and 4(*iii*), the nerve 100 will press against the sMEA 20 thereby drawing the nerve 100 and sMEA 20 into a first cavity portion or upper entry portion 7 of the printed microclip 2.

As shown in FIGS. 4(*ii*)-(*iii*), an adjustment tool (tungsten point) 3 can be inserted into the manipulation hole 10 of the printed microclip 2 to advance the microclip 2 towards the nerve. Thus, the nerve 100 is smoothly entered into the upper entry portion 7 and then to a second lower cavity portion or lower seating portion 9 of the printed microclip 2 without significantly injuring the nerve 100.

As shown in FIG. 4(*iv*), the nerve 100 is wrapped with the electrode pads 24 while seated in the second cavity or seating portion 9. Further, the tool 3 can then be removed from the manipulation hole 10 (FIG. 4(*v*)). As shown in the right lower corner of FIG. 4, the stimulating and recording electrode pads 24 are wrapped around the nerve 100 on both sides of the nerve 100. In addition, as described above, the wrap-on-implant allows for placing the electrode pads 24 at arbitrary points on the circumference of the nerve 100 and eliminates the need for suturing or surgical adhesives to stabilize the preparation. Thus, as described above, discrete signals can be recorded on the circumference of the nerve, which is a significant improvement over related art interfaces that only record on one side surface of the nerve.

Next, FIG. 5 includes overviews illustrating an experiment of implanting a μcPNI on a tracheosyringeal nerve (TSN) of a zebra finch according to an embodiment of the present invention. In more detail, FIG. 5(*a*) illustrates the microclip 2 implanted on the TSN 100 of the zebra finch. Further, FIG. 5(*b*) is a photomicrograph of the μcPNI implanted on the TSN 100 of the zebra finch.

As shown in FIG. 5(*a*), the TSN 100 runs along the length of the songbird trachea and terminates at the syrinx. The TSN 100 has a diameter of approximately 150 μm and includes both afferent and efferent fibers. The printed microclip 2 secures the TSN 100 while simultaneously wrapping electrode pads 24 of an electrode array 22 around the circumference of the nerve 100. Further, the nerve 100 is grasped and retained in the lower seating portion 9 without causing damage to the nerve 100. As shown in FIGS. 5(*a*) and (*b*), the size or scale of the μcPNI is comparable to that of the implant target (e.g., the nerve 100).

Next, FIG. 6 illustrates the size of the μcPNI according to an embodiment of the present invention compared with a related art Cortec cuff. In addition, the red dot in FIG. 6 also represents a diameter of the nerve 100 (e.g., 150 μm). As shown, the μcPNI is much smaller in size compared to the related art Cortec cuff. Thus, the μcPNI according to embodiments of the present invention can minimize progressive neuropathy caused by stretching or rubbing of the nerve or surrounding tissue, while still having more electrodes than related art cuff type electrodes. The μcPNI also enables improved studies of PNS function over developmental, disease, and restorative processes, and supports generation of bioelectronic therapeutics centered on sensing and modulating peripheral circuit functions.

Figure 7:
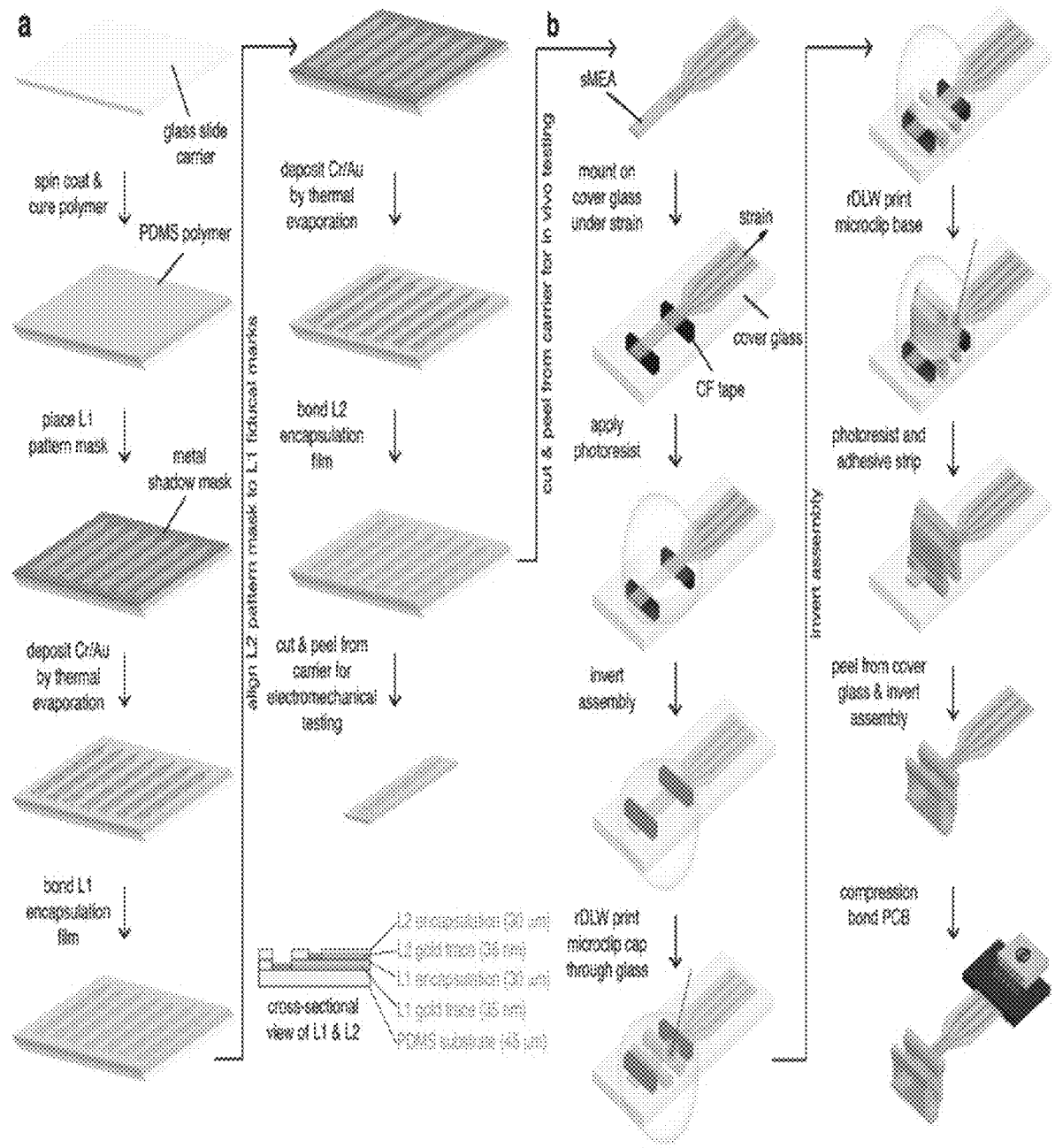
FIG. 7 is a flow diagram illustrating a fabrication process for the μcPNI according to an embodiment of the present invention.

Next, FIG. 7 illustrates a process of manufacturing a μcPNI according to an embodiment of the present invention. As shown in the second column of FIG. 7(*a*), the sMEA 20 according one embodiment includes a sequence of five material layers: 1) a PDMS or elastomeric substrate (e.g., with a thickness of 45 μm), 2) microcracked gold electrodes (e.g., with a thickness of 35 nm and from U.S. Pat. No. 7,491,892) on the PDMS substrate, 3) a PDMS encapsulation on the microcracked electrodes (e.g., with a thickness of 30 μm), 4) microcracked gold electrodes on the PDMS encapsulation (e.g., with a thickness of 35 nm), and 5) a PDMS encapsulation on the electrodes (e.g., with a thickness of 30 μm). Thus, the layer L1 in FIG. 2 includes the L1 gold trace film and the L1 encapsulation, and the layer L2 in FIG. 2 includes the L2 gold trace film and the L2 encapsulation. Thus, the sMEA 20 in this example is a bi-layer sMEA (e.g., layers L1 and L2). The microcracked electrodes can also be other types of flexible conductor materials such as nanoparticle conductive inks, metal nanowires, etc. that are flexible and stretchable to flex and stretch with the PDMS or elastomeric substrate.

In more detail, as shown in FIG. 7, a glass slide carrier is provided and a PDMS polymer or elastomeric polymer, for example, is spin coated and cured on the glass slide carrier. A pattern mask such as a metal shadow mask is then used to outline microelectrodes on the PDMS polymer. Other methods such as deposition of a blanket gold film followed by removal of the unwanted areas of the gold can also be used for patterning the microelectrodes. The metal shadow mask acts as a stencil for the Cr/Au electrodes to be deposited within the lines. A thermal evaporator is then used to deposit the Cr/Au.

The microelectrodes can then be formed on the PDMS polymer, for example, by depositing Cr/Au using a method of thermal evaporation, for example. An encapsulation film is then deposited on the formed microelectrodes such that the microelectrodes are encapsulated by the PDMS film with contact holes to the recording/stimulating pads 24 and contact pads 28.

A layer 2 (L2) mask is then aligned with fiducial marks on layer L1, and the electrodes on layer 2 (L2) are formed, for example, by depositing Cr/Au using a method of thermal evaporation, for example. The layer 2 (L2) electrodes are then encapsulated with a PDMS film as was done for the layer L1 electrodes. The glass slide carrier is then removed. For example, the formed layers L1 and L2 and the PDMS polymer substrate can peeled from the glass slide carrier. As shown in FIG. 7, the remaining layers and substrate can then be cut into individual sMEAs for electromechanical testing, in vitro and in vivo testing, etc.

In more detail, in one embodiment, the microcracked gold film for the layer L1 electrodes was deposited by sequential thermal evaporation of 3 nm Cr, 35 nm Au, and 3 nm Cr thickness through a shadow mask on a 45 μm thick PDMS substrate on the glass slide carrier. The L1 structures were encapsulated by transfer bonding with a 30 μm thick PDMS layer with pre-patterned holes exposing the electrode recording/stimulating pads 24 and contact pads 28. The L2 structures were similarly defined in gold and chromium via shadow masks and encapsulated by a second pre-patterned 30 μm thick PDMS layer.

Also, preferably only one side of the microclip cap includes the electrode clamp 4 printed flush with the surface of the tensioned sMEA 20 (see FIG. 8). As shown in FIG. 7, following printing, the entire assembly is submerged in nitromethane, for example, to strip both the unpolymerized photoresist and the mounting adhesive of the carbon fiber tape, releasing the sMEA 20 from tension. Other stripping methods may also be used. Upon strain relaxation and reversal of Poisson compression, the sMEA 20 is thicker than the gap between opposing sides of the printed clamp (approximately 60 μm), and therefore the sMEA 20 is mechanically fixed at the end distal to the PCB while the proximal segment remains free to slide within the microclip 2. Thus, the rigid microclip 2 can be robustly attached to the soft electrode array without the need for additional manual assembly or a post-printing adhesive application.

That is, one example of the fabrication steps includes mounting the stretchable electrode array under tension on a thin optical glass substrate (e.g., 24 mm×60 mm, #0-thickness cover glass, Gold Seal) with 250 μm-thick double-sided acrylic tape (3M), and depositing a drop (approximately 0.5-2 μL) of liquid acrylic photoresist (e.g., IP-Dip, Nanoscribe, GmbH) over and beneath the recording electrode array. Then, the glass and sample are inverted and the microclip cap is printed through the optical glass substrate using a two-photon-polymerization-based, dip-in resonant direct laser writing (rDWL) process. The glass substrate and sample are then righted (inverted), and the base of the microclip is printed with the rDWL process. Further, the photoresist was developed and tape adhesive dissolved by submerging the glass substrate, electrode, and nanoclip in nitromethane (e.g., Sigma Aldrich) for 20 min, and the entire device rinsed in methoxynonafluorobutane (e.g., Novec 7100; 3M) to remove trace solvent residue. The assembly is then removed from the glass slide and compression bonded to a connectorized PCB as described above. The mechanical design of the microclip can be performed using Solidworks (Dassault Systèmes). The section of the sMEA with the contact pads (proximal section) was then compression-bonded between two custom PCBs with a 16-channel Omnetics connector (A79040-001).

As shown in FIG. 7(b), the sMEA is then mounted on a cover glass under strain. The strain direction is shown in FIG. 8. In more detail, the microclip 2 is robustly integrated with the soft and stretchable elastic microelectrode array 20. An embodiment of the present invention advantageously uses the Poisson compression of PDMS under strain to insert the sMEA into and secure one end of the sMEA to the printed microclip 2. In more detail, the sMEA is mounted under longitudinal tension onto a cover glass carrier with carbon fiber (CF) tape, for example. The applied strain reduces a thickness of the sMEA 20 consistent with the Poisson effect, and the microclip cap and base can then be printed on opposing sides of the tensioned sMEA 20.

In particular, FIG. 8 is a schema for clamping the microclip 2 onto the sMEA 20. As shown, FIG. 8(a) illustrates the μcPNI in a final assembly state, and FIG. 8(b) is a cross-sectional view of the μcPNI illustrating a teeth-like printed clamp 4 on only one side and the sMEA 20 in a strained state that reduces the thickness of the sMEA. Finally, FIG. 8(c) illustrates the state of the μcPNI following the release from strain, in which the sMEA 20 thickness is restored and thus mechanically fixed in the printed clamp 4. In FIG. 8, the electrode clamp 4 is 3D printed flush with a surface of the tensioned electrode array at only one leg portion of the microclip 2.

As shown in FIG. 8, wherein the microclip includes a lower base portion; a first upper leg portion extending from the lower base portion; and a second upper leg portion extending from the lower base portion and spaced apart a predetermined distance from the first upper leg portion to form the U-shape. Further, the first upper leg portion is positioned closest to the distal end of the stretchable microelectrode array and the second upper leg portion is positioned closest to the proximal end of the stretchable microelectrode array. In addition, the predetermined distance between the first upper leg portion and the second upper leg portion is substantially equal to a sum of a diameter of the nerve and twice a thickness of the stretchable microelectrode array. Further, as shown in FIG. 8, each of the first upper leg portion and the second upper leg portion includes an opening for passing the stretchable microelectrode array through the first and second upper leg portions of the microclip. Also, the first upper leg portion includes a first base portion and a first cap portion at the upper entry portion, the second upper leg portion includes a second base portion and a second cap portion at the upper entry portion, the second base portion of the second upper leg portion includes at least a first printed electrode clamp protruding towards the second cap portion, and the second cap portion of the second upper leg portion includes at least a second printed electrode clamp protruding towards the second base portion to clamp the stretchable electrode array to the microclip. In addition, the first and second printed electrode clamps are spaced apart from one other by a distance equal to the thickness of the stretchable electrode array under strain.

Figure 9:
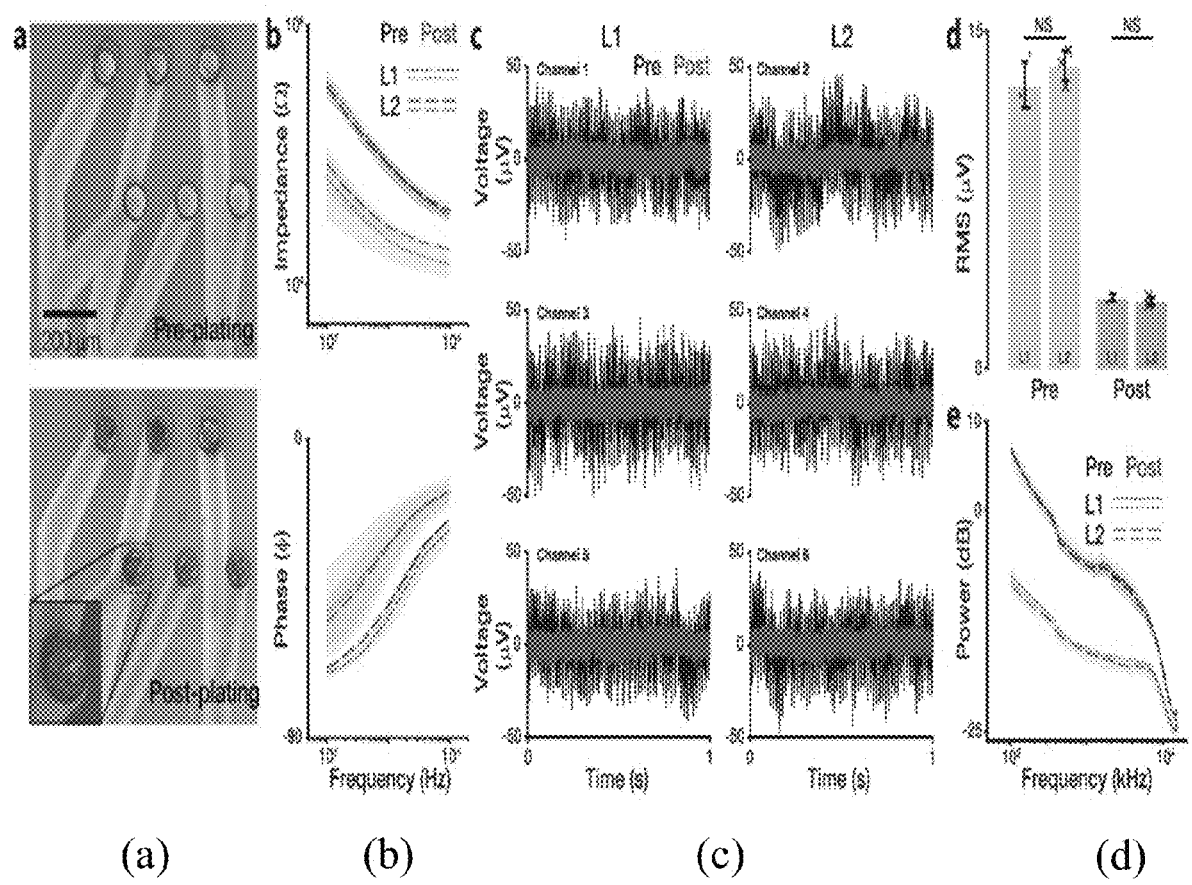
FIG. 9 includes photomicrographs of μcPNI electrodes sites before and after electroplating and graphs illustrating electrically characteristics of the electrode array according to an embodiment of the present invention.

Next, FIG. 9 includes photomicrographs of μcPNI electrodes sites before and after electroplating and graphs illustrating electrically characteristics of the electrode array according to an embodiment of the present invention. In particular, FIG. 9(a) includes photomicrographs of μcPNI electrode sites before (top) and after (bottom) electroplating with platinum (Pt) black. Other plating solutions can be used such as PEDOT, IrOx, etc.

The inset lower photomicrograph in FIG. 9(a) is a zoomed view of a plated electrode stimulating and recording pad 24. The recording sites 24 of the electrodes were electroplated with platinum (Pt) black to reduce the electrode impedance, and thus the noise of the recording and the size of the stimulation artifact.

In addition, FIG. 9(b) is an electro-impedance spectroscopy of the six channels on the μcPNI before and after electroplating with Pt black. The mean of layers L1 and L2 electrodes are shown as dotted and dashed lines, respectively, and the standard deviation across a layer is indicated by shaded regions. FIG. 9(c) includes graphs illustrating baseline noise recordings of the six μcPNI channels before and after Pt black electroplating.

Further, FIG. 9(d) is a graph illustrating a root mean square (RMS) of baseline noise across all channels (n=3 each on layers L1 and L2) before and after electroplating. In FIG. 9(d), markers are used to identify individual channels, and bars and error bars are used to denote mean±std across n=3 channels. In addition, N.S.=not significant (P=0.4 and 0.7, respectively) in FIG. 9(d). Also, FIG. 9(e) is a graph illustrating the mean power spectrum of baseline noise across channels before and after electroplating. The mean of the L1 and L2 electrode pads are shown as dotted and dashed lines, respectively, and the standard deviation across a layer is indicated by shaded regions.

As-fabricated electrodes have a high impedance (>1 MΩ) due to their small surface area (approximately 5000 μm²), which contributes to a higher noise for recordings and artifacts for stimulation. To reduce the electrode impedance, platinum black was electrodeposited on the electrode surface (FIG. 9(a)). As shown in FIG. 9(b), the impedance spectroscopy of the electrodes before and after plating showed a larger than tenfold reduction in impedance (at 1 kHz) across all electrodes on both L1 and L2 layers from 465±200 to 20±7 kΩ with no significant difference between electrode layers pre- and post-plating (P=0.3 and P=0.7, respectively). The comparable measurements of the two electrode layers (P=0.1) indicates that a slight misalignment (approximately 10 μm in the top of FIG. 9(a))) between the electrodes and encapsulation layer openings has no appreciable effect on impedance and recording measurements.

Thus, aligning and bonding PDMS-based multi-layer devices with high accuracy over large distances (here: >40 mm from recording sites to contact pads to PCB) is not needed. As shown in FIGS. 9(c) and 9(d), the reduction in impedance was accompanied by a reduction in peak-to-peak voltage (VPP) noise from >60 μV to <10 μV (bandwidth: 0.001-7.5 kHz) that was consistent across channels and not significantly different between electrode layers (P=0.7). This baseline noise is desirable as the nerve signals are in the range of tens to hundreds of μV. In FIG. 9(e), a comparison of the mean power spectrum of the baseline noise before and after electroplating indicates a broad decrease in noise power in the 0.5-6 kHz frequency band associated with multi-unit neuronal activity, without any significant difference between electrodes on both layers.

Figure 10:
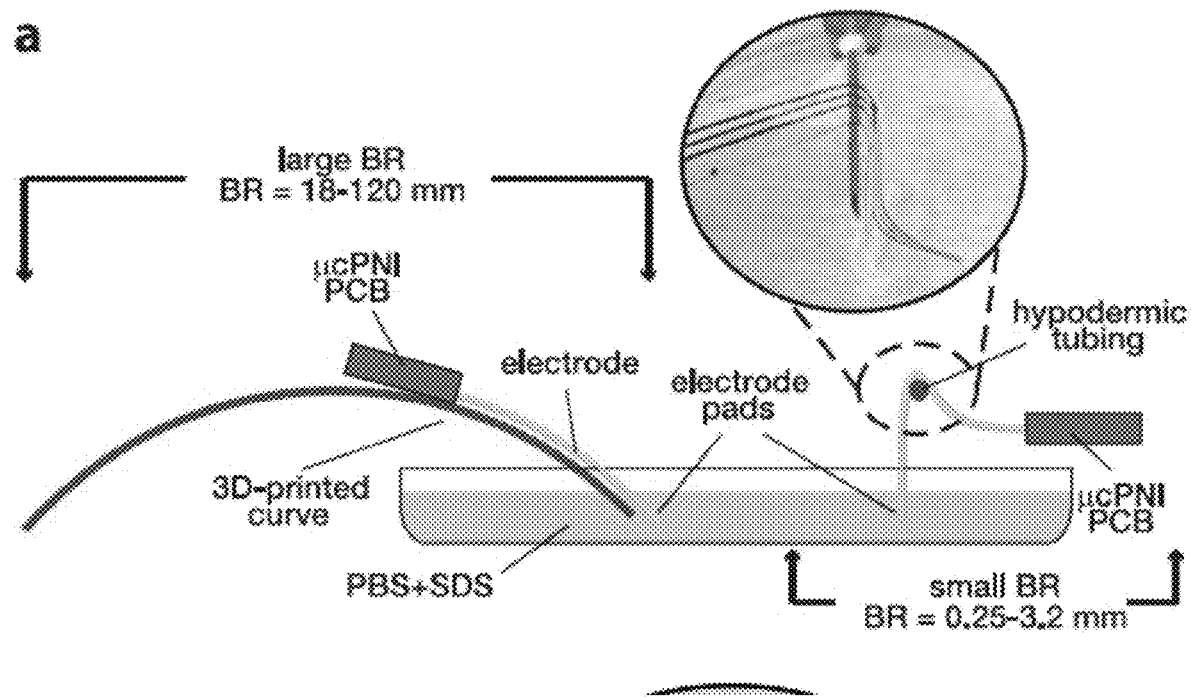
FIG. 10 includes overviews of an experimental setup to access a bending strain, bending fatigue, and charge injection limit of the electrode array and a corresponding electrode impedance graphs according to an embodiment of the present invention.
Figure 10:
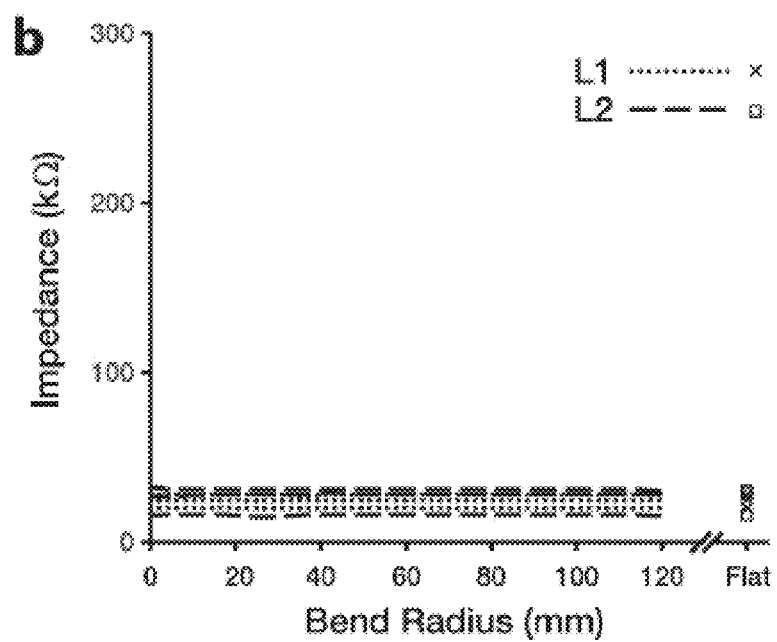
Figure 10:
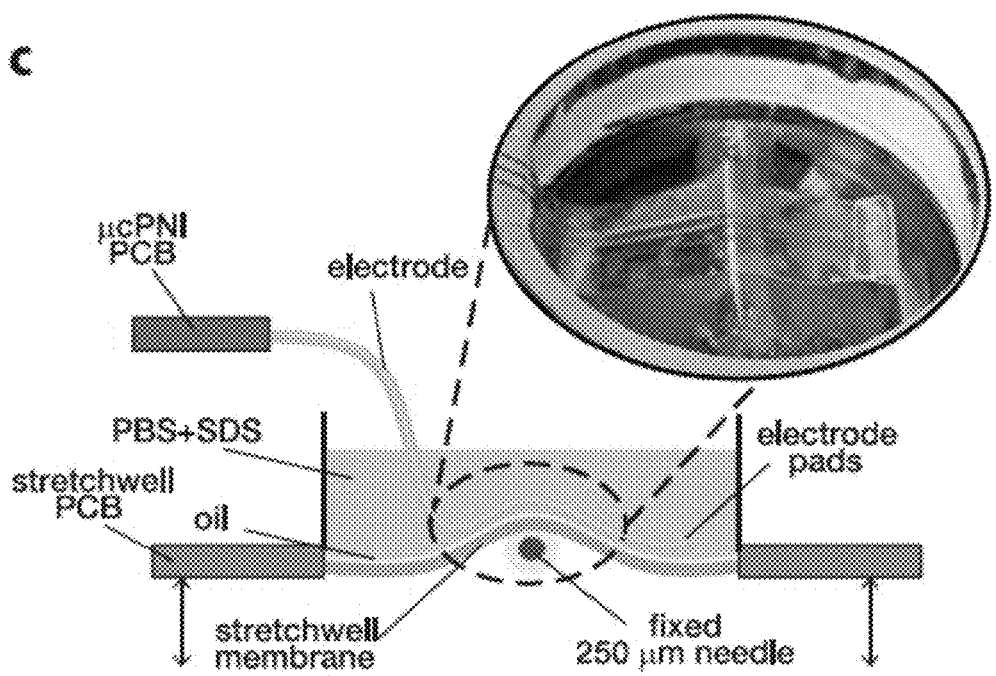
Figure 10:
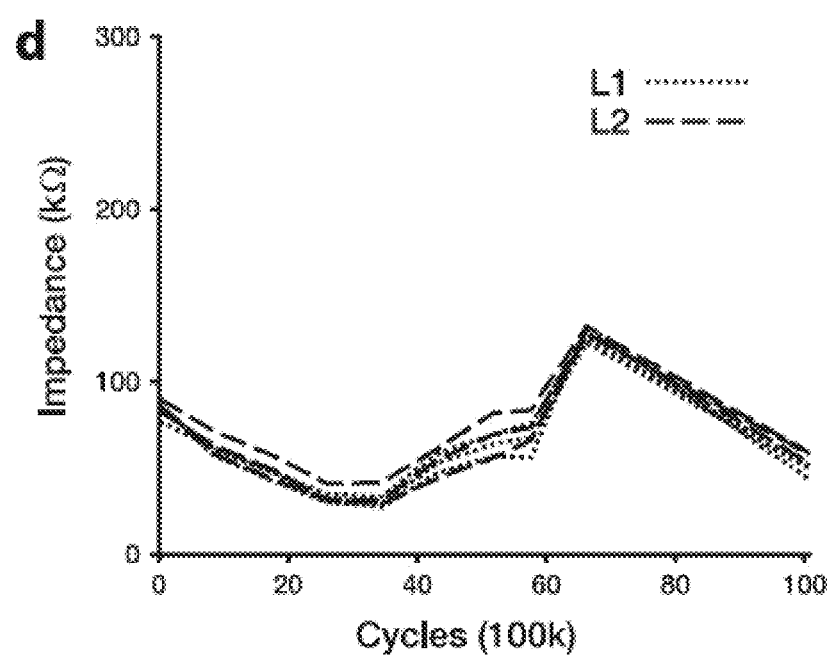
Figure 10:
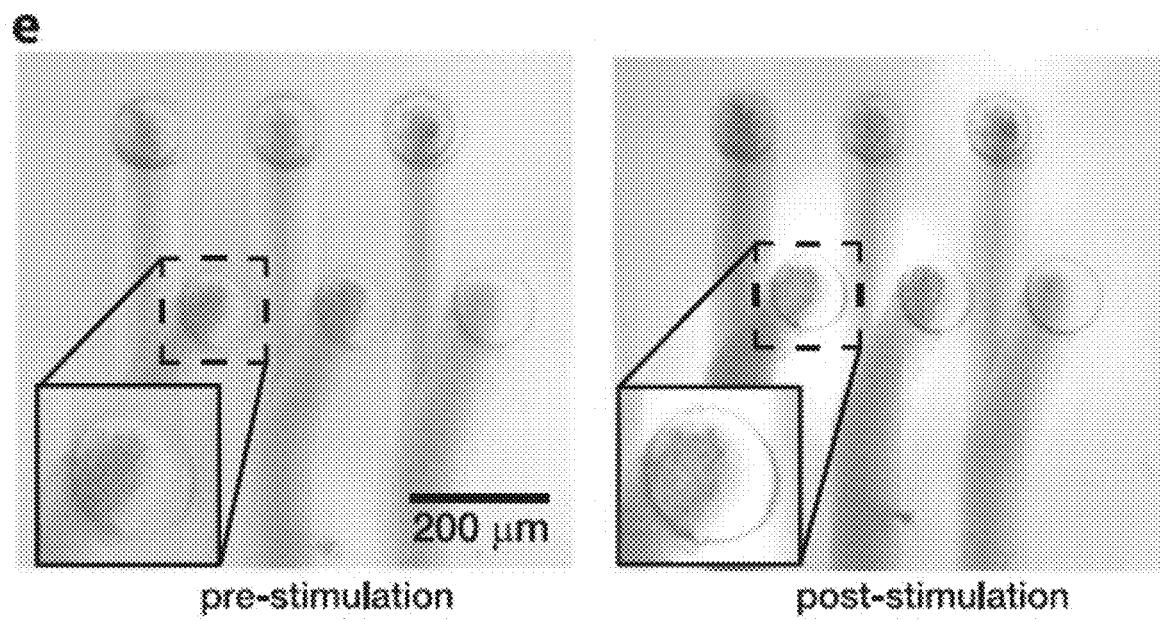
Figure 10:
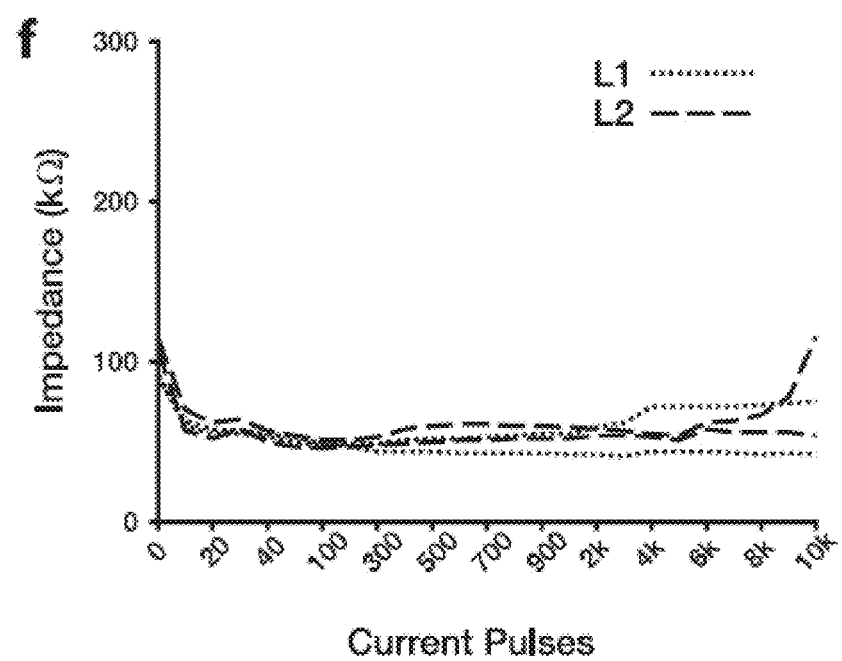

Next, FIG. 10 illustrates an experimental setup and corresponding experimental results of bending strain and bending fatigue of the electrode array 22 of the sMEA 20. In particular, FIG. 10(a) is an overview of an experimental setup to assess a bending strain of the electrode array 22, and FIG. 10(b) is a graph illustrating the electrode impedance versus bending radius with layers L1 and L2 electrode pads shown as dotted and dashed lines, respectively, and markers identify individual channels. FIG. 10(c) is an overview of an experimental setup to assess bending fatigue of the electrode array, and FIG. 10(d) is a graph illustrating electrode impedance versus bending cycles with layers L1 and L2 electrode pads shown as dotted and dashed lines, respectively.

In more detail, the bending strain (ε) in the electrodes is proportional to the distance of the gold film from the neutral plane, $d_N$, and inversely proportional to the bending radius, BR ($\varepsilon = d_N BR^{-1}$). In the microclip section of the μcPNI, the bending strain is highest due to the small BR when the leads are wrapped around small nerves. To reduce the bending strain, the thickness of the PDMS substrate and the encapsulation layers for L1 and L2 are preferably selected so as to minimize $d_N$ (e.g. a thickness of 30 μm for each layer atop a 45 μm thick substrate, as shown in FIG. 7). Furthermore, the bending strain on the gold film is in the microclip section is compressive by design, and a resistance of a single layer microcracked gold conductors is not appreciably altered during static bending for strains up to at least 15% for electrode leads in compression. The impedance of all six electrodes on several μcPNI pre-plating, post-plating, in vivo while implanted, and post-explantation were measured.

The electrode impedance was not appreciably altered after three weeks of implantation, that is, the impedance post-plating (20±7 kΩ) and post-explantation (29±10 kΩ) are comparable. The impedance in vivo is higher (75±13 kΩ) compared to before implantation (post-plating) and post-explantation, but remains below 100 kΩ for all electrodes. The difference in ionic strength of the medium and the confinement of the recording sites between the microclip and the nerve contribute to this increase in impedance.

In the section of the μcPNI between the microclip and the PCB, the electrode leads can be in tension or compression depending on the bending direction induced by body dynamics. In tension, the resistance of microcracked conductors increases exponentially with bending strain, and bending causes a larger increase in resistance for the same strain compared to stretching. To minimize the effect of bending on electrode impedance and recording noise, the gold electrodes on the μcPNI are, preferably by design, close to the neutral plane to minimize strain and in compression (L2 only) when wrapped around the nerve.

To validate the robustness of the bi-layer μcPNI, and as shown in FIG. 10(a), the electrode array was bent in tension at a BR ranging from 250 μm to 120 mm while the impedance at 1 kHz was measured in phosphate-buffered saline (PBS) and sodium dodecyl sulfate (SDS) (e.g., SDS of 40 mM, Sigma Aldrich). The experiment was performed four separate times and averaged for each channel. FIG. 10(b) is a plot of the impedance of all six channels versus the BR. As shown, the impedance for a given channel does not change appreciably with BR. That is, there is no significant difference between electrodes on layers L1 and L2 (one-way ANOVA: P=0.51).

In addition, a single layer with microcracked gold electrodes can be stretched by more than 20% for over a million cycles. Thus, an experiment was performed to determine the effects of bending fatigue on the impedance of a bi-layer μcPNI. In particular, as shown in FIG. 10(c), the leads of the electrodes were continuously wrapped and unwrapped over 1 million cycles around a 250 μm radius hypodermic needle, and the electrode impedance (at 1 kHz) was measured periodically. A BR of 250 μm was chosen because the electrodes are unlikely to experience higher bending strain (smaller BR) in the section between the microclip and the PCB during implantation. FIG. 10(d) is a plot illustrating the impedance of all six channels versus the number of bending cycles. As shown, there is no appreciable bending fatigue over the course of 1 million bending cycles as no sustained increase in impedance is observed.

Further, the variation in impedance over 1 million bending cycles (90 kΩ±35 kΩ) are random measurement variances caused by the sample being located in an incubator for two weeks. However, no significant difference in the impedance of electrodes on different layers was found (one-way ANOVA: P=0.078).

In addition, the charge injection limit is the maximum amount of charge (current×time) that can be injected without causing irreversible damage to the electrode. Accordingly, to determine the charge injection limit for the μcPNI, a 110 μA constant current bi-phasic stimulus (at 1 Hz and 133 μs phase$^{-1}$) was generated out-of-phase by two of the six Pt black-coated μcPNI electrodes (80 μm diameter and 22 mA mm$^{-1}$ charge density) in a PBS solution. Further, 10000 biphasic, bipolar stimulating pulses were first injected through two L1 electrodes and then two L2 electrodes for a total of 20000 pulses.

FIG. 10(e) includes photomicrographs of the μcPNI electrode recording/stimulation sites before and after injecting the 10,000 pulses at 110 μA for a duration of 133 μs illustrating minor metal degradation in the observed electrode. FIG. 10(f) is a graph illustrating the impedance (at 1 kHz) of the four stimulated electrodes in PBS over the course of 10000 stimulation pulses.

As shown, the impedance of all electrodes decreases from about 100 kΩ to about 50 kΩ over the first 20 stimulation pulses possibly due to removal of contamination from the electrode surface by desorption or oxidation of contaminants caused by the current pulses. After the first 20 pulses, the impedance of electrodes on layers L1 and L2 remained constant over 10000 pulses, and no significant difference in the impedance of electrodes on different layers occurred (one-way ANOVA: P=0.074).

Initial testing also injected 200 μA constant current biphasic stimulus (at 1 Hz and 200 μs phase-1; and 40 mA mm$^{-1}$ charge density) through μcPNI layers L1 and L2 electrodes to investigate the in vivo stimulation conditions. Electrodes in these tests demonstrated significant metal degradation and increases in impedance between 5000-10000 pulses. Therefore, in one embodiment, the size of the stimulating electrodes are preferably significantly larger so the current density will be lower. Thus, the number of pulses that can be injected without damaging the electrodes increases. In another embodiment, the size of the stimulating electrodes are similar in size to the recording electrodes.

The electrical and mechanical stability of the μcPNI is advantageous for in vivo recording and modulation of small nerves within a biomechanically dynamic environment. During implantation in vivo, the leads of the μcPNI experience a static bending strain in the section that is in contact with the microclip, and multi-axial mechanical deformation in the section between the microclip and the PCB in response to the songbird's natural body movements.

It is advantageous that these mechanical deformations do not affect the impedance, hence recording and stimulation properties, of the electrodes. FIG. 10 illustrates results of a benchtop test of a μcPNI to confirm its advantageous safe and effective chronic implantation in small animals, with a particular emphasis to detect differences between electrodes on the two layers L1 and L2.

Therefore, referring to FIGS. 9 and 10, post-electroplating impedance and recording noise in PBS were measured (e.g., using an Intan RHS 128ch recording/stimulation controller, Intan Technologies) at 1 kHz against a Pt counter electrode inside a custom-built Faraday cage connected to a PCB ground. The target impedance was 1000 kΩ>Z>1 kΩ, and electrodes were not considered functional if the impedance was outside this range.

In addition, the impedance of all six electrodes was measured while bending the leads of the μcPNI array around spherical segments that were 3D printed with acrylonitrile butadiene styrene (ABS) for BR 18-120 mm, around the shanks of drill bits for BR 3.2-0.8 mm, and around the shaft of a hypodermic needle for BR 0.25 mm. The electrode array was plasma treated (30 s) and immersed in PBS and bent over the segment (FIG. 10(a)). The impedance was measured (e.g., using an Intan RHS 128ch recording/stimulation controller, Intan Technologies) inside a Faraday cage as described above, with the cage connected to the PCB ground pad 44, and a Pt counter electrode connected to the PCB reference pad 42 (FIG. 3). Three impedance measurements were taken and averaged for each of the fourteen bending radii ranging from 250 μm to 120 mm.

The distal end of the μcPNI (the section with the recording sites) was bonded to a PDMS stretchwell with a small amount of uncured PDMS (same as for the substrate) followed by curing for at least 12 h at 60° C. (FIG. 10(c)). A stretchwell includes a PDMS membrane that was sandwiched between two PCBs with circular cutouts in the center and a polycarbonate well that was glued to the top PCB. The well was filled with a PBS solution, and the distal end of the μcPNI with the PCB was placed outside of the stretchwell. With this arrangement, the μcPNI was exposed to a small amount of tensile strain in addition to bending strain, which realistically reproduces the mechanical forces that the μcPNI will experience in vivo. For fatigue testing of the μcPNI array, the stretchwell was mechanically raised and lowered around the shaft of a hypodermic needle with a 250 μm radius (FIG. 10(c)). One bending cycle included wrapping and unwrapping the μcPNI leads at a 45° angle around the needle shaft. A total of 1,000,000 cycles were performed at 1 Hz and the electrode impedance in PBS was measured using the Intan RHS 128ch recording/stimulation controller periodically over the course of two weeks.

Further, the Pt black coated electrodes of the μcPNI were immersed in PBS and connected to an Intan RHS 128 channel recording/stimulation controller. Then, 10000 biphasic, out-of-phase bipolar stimulating pulses were injected at 1 Hz at a stimulus amplitude (110 μA) and a duration (133 μs). The electrode impedance was then measured using the Intan RHS 128ch recording/stimulation controller before and after every 10 stimulation pulses for the first 100 pulses, after every 100 stimulation pulses up to 1000 pulses, etc. (FIG. 10(f)).

Figure 11:
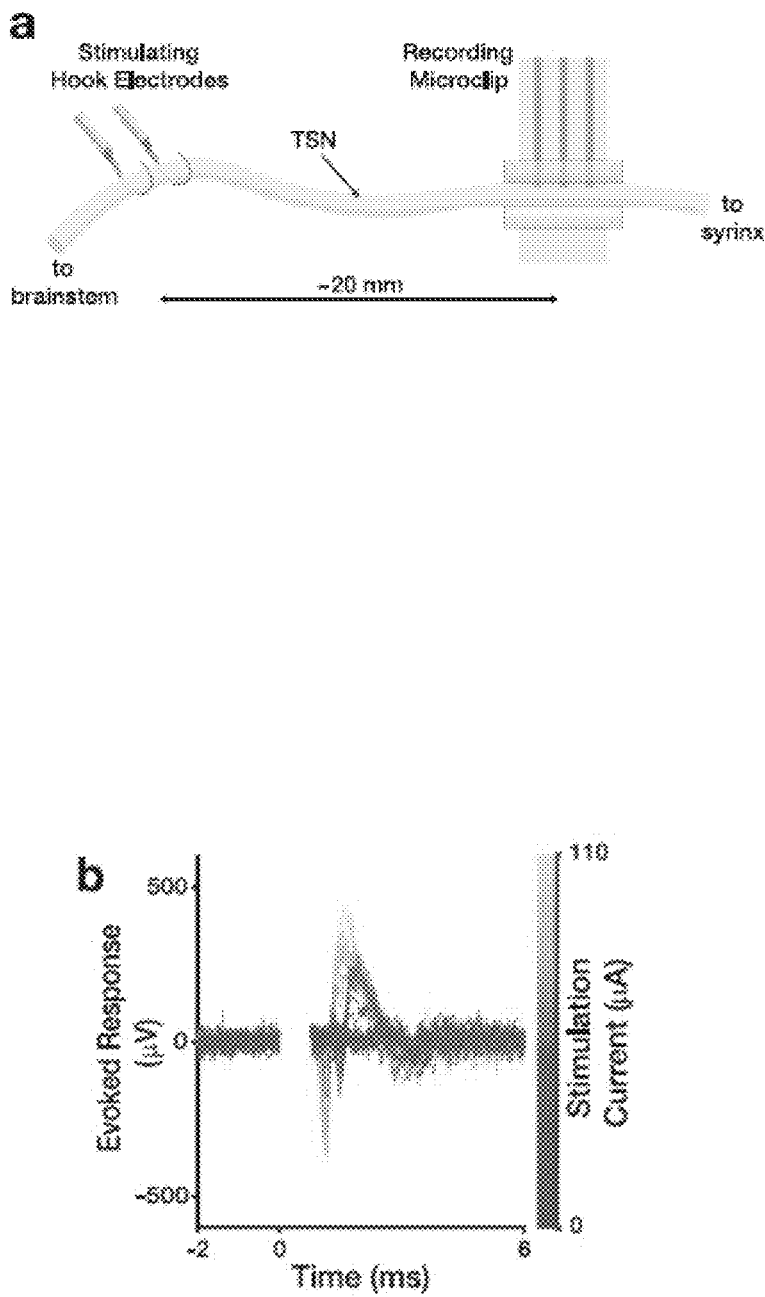
FIG. 11 includes an overview illustrating in vivo recording by a μcPNI of stimulation-evoked nerve activity according to an embodiment of the present invention.
Figure 11:
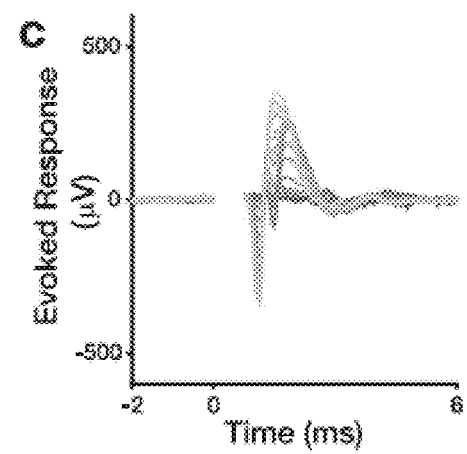
Figure 11:
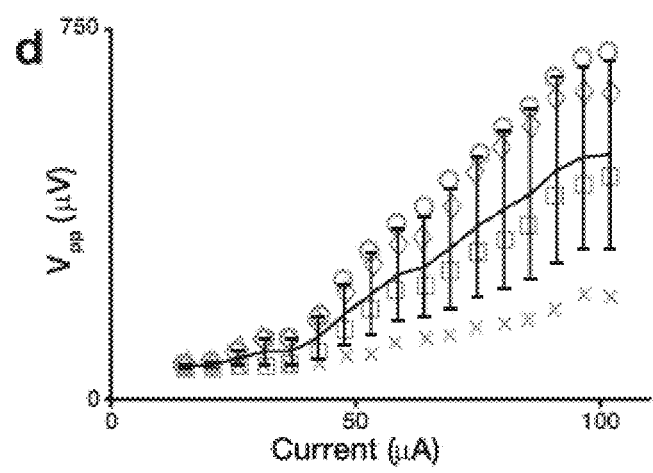
Figure 11:
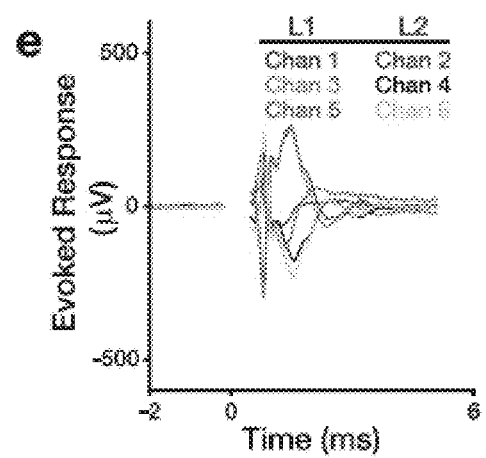
Figure 11:
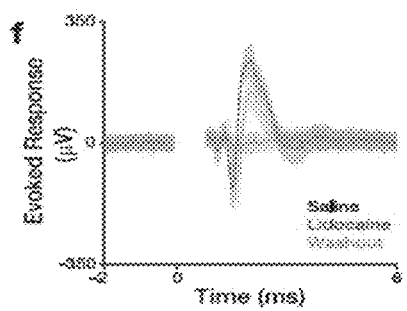
Figure 11:
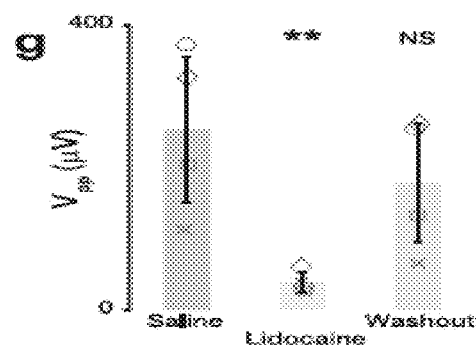

Next, FIG. 11 includes an overview of an experiment of acute in vivo recording of stimulation-evoked nerve activity according to an embodiment of the present invention. In particular, FIG. 11(a) is a schema for acute recording of evoked responses in which a current-controlled stimulation was delivered via bipolar silver hook electrodes, and evoked responses were recorded by a μcPNI according to an embodiment of the present invention placed approximately 20 mm caudally (two approximately 2 mm segments of the right-side TSN approximately 20 mm apart were dissected from surrounding tissue). FIG. 11(b) is a graph illustrating representative examples of responses evoked by graded stimulation currents in which stimulations of 10-110 μA of biphasic pulses and a 200 μs phase$^{-1}$ were applied at t=0 ms. Each line illustrates the single-trial response, and the line color indicates stimulation current as indicated in the color bar. FIG. 11(c) is similar to FIG. 11(b), but further illustrates the mean response across trials (16-64 trials) at binned stimulation currents (a bin width=5 μA). Each line shows the mean response, and the line color indicates stimulation current as in FIG. 11(b).

Also, FIG. 11(d) is a graph illustrating an evoked response peak-to-peak voltage (Vpp) as a function of stimulation intensity. In this graph, each data point indicates the mean across trials within an animal (16-64 trials) with each gray symbol identifying individual birds, and black lines and error bars indicate the mean and standard deviation across animals (n=4 birds). FIG. 11(e) is a graph illustrating representative examples of evoked response waveforms recorded simultaneously on each electrode. A stimulation of 67 μA of biphasic pulses at 200 μs phase$^{-1}$ was applied at t=0 ms. Each line shows the mean response across trials (n=64 trials), and the line color indicates the recording channel.

FIG. 11(f) is a graph illustrating an example of evoked responses recorded before, during, and after local lidocaine application. A stimulation of 64 μA of biphasic pulses at 200

µs phase$^{-1}$ was applied at t=0 ms. Each line and shaded region show the mean±std for n=24 trials. FIG. 11(g) is a graph illustrating an evoked response Vpp across the conditions shown in FIG. 11(f). Each data point indicates the mean across 24 trials within an animal, the grey symbols identify individual birds, and the bars and error bars denote mean±std across n=4 birds per condition. **P<0.01 Repeated-measures ANOVA, P=0.007; Dunnett's test, P=0.009.

To confirm the µcPNI acute recording performance, evoked compound responses were recorded from the TSN in anesthetized zebra finches. The results of the experiment confirm the successful performance of the µcPNI in sensing and modulating small nerve activity. In more detail, as described above, the µcPNI was implanted on the zebra finch TSN, which is an avian hypoglossal analog that innervates the songbird vocal organ (i.e., the syrinx). The TSN is an ideal model in which to characterize PNI technologies due to its surgical accessibility and physiological homologies to mammalian sensorimotor nerves of therapeutic interest. In addition, the multi-month stereotypy of singing-related TSN activity patterns and their high temporal correlation with vocalization provide a strong benchmark against which to assess chronic performance and stability.

Similar to estimates of conduction velocities in 5-8 µm nerve fibers, the primary components of evoked responses 0.75-4 ms after stimulation onset were identified. Also, graded evoked response curves were obtained by varying the stimulation current amplitude (FIGS. 11(b) and 11(c)). Across experiments in n=4 birds, Vpp illustrates a sigmoidal relationship with increasing stimulation current (FIG. 11(d)), consistent with standard models of fiber recruitment.

FIG. 11(e) illustrates the common mode subtracted response waveforms were also unique across channels. This uniqueness stands in marked contrast to prior studies showing highly correlated waveforms across closely spaced channels on one side of an implanted nerve and illustrates that even within small geometry spatially distributed recording electrodes can access distinct subcomponents of the evoked response.

To confirm the neuronal origin of these responses, 2% lidocaine was applied at the stimulating site to reversibly block nerve conduction (FIG. 11(f))). Across experiments (n=4 birds shown in FIG. 11(g)), lidocaine abolished evoked responses with Vpp declining significantly from saline controls (P=0.009), and subsequent washout with saline restored response amplitudes not to be significantly different from control (P=0.29).

Figure 12:
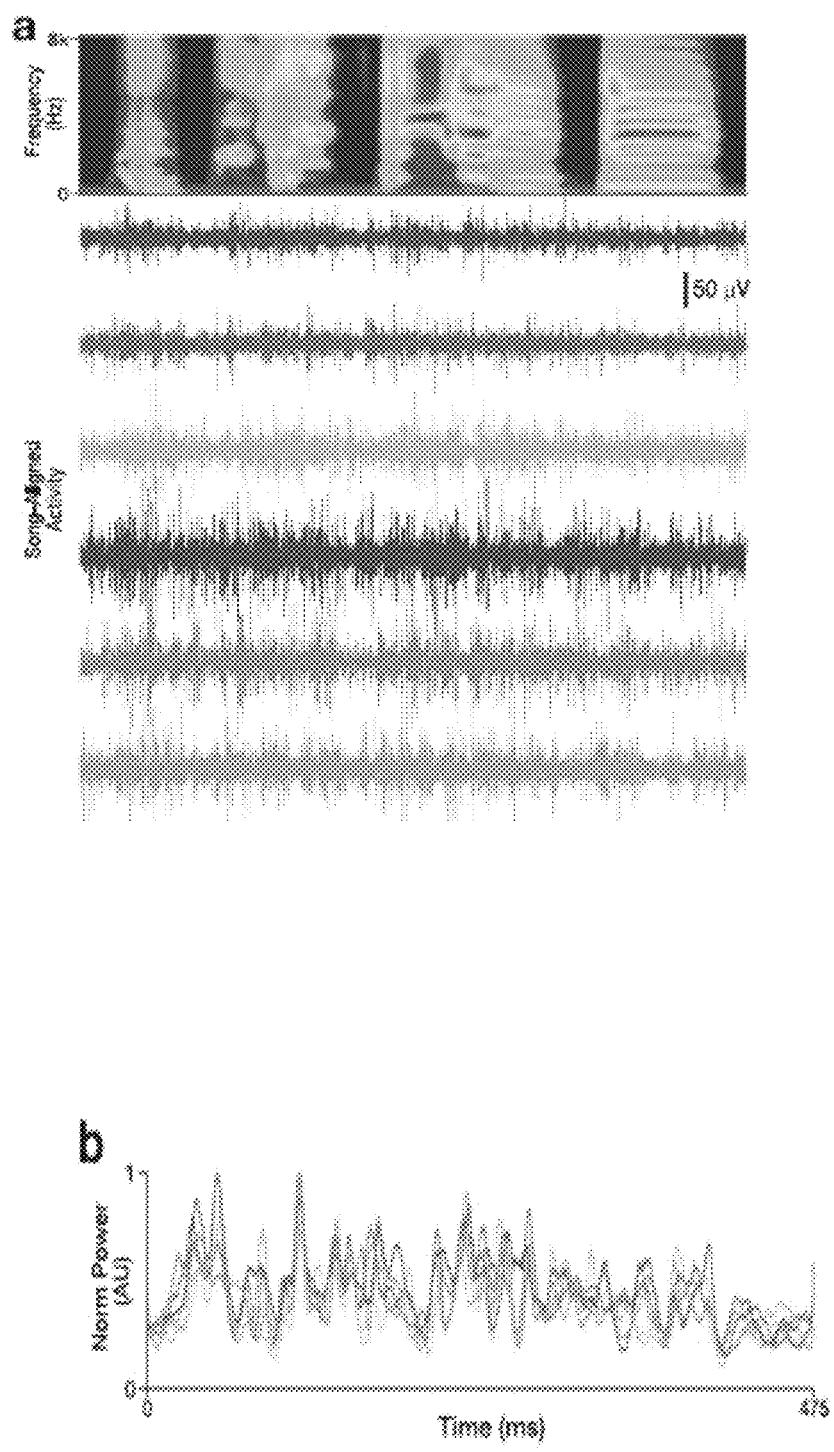
FIG. 12 includes an overview illustrating in vivo recording by a μcPNI of spontaneous nerve activity according to an embodiment of the present invention.
Figure 12:
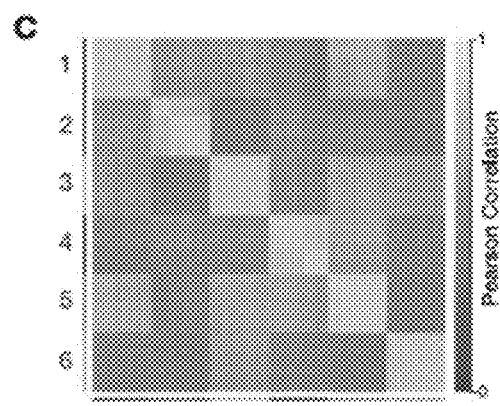
Figure 12:
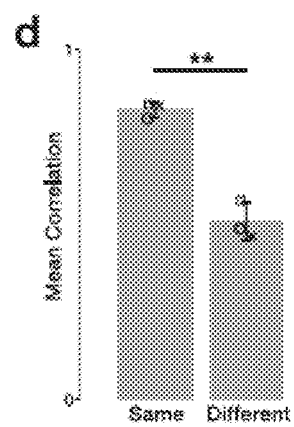
Figure 12:
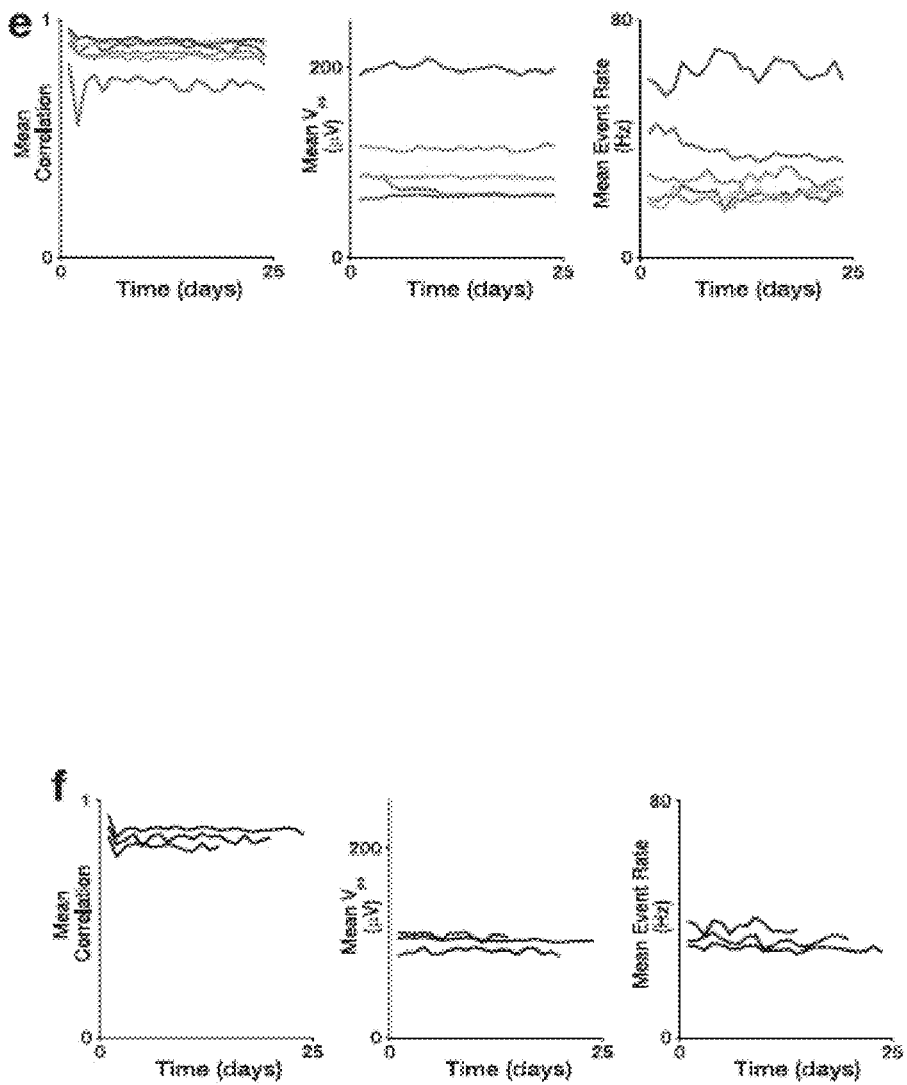

Next, FIG. 12 includes graphical recording results of spontaneous electrical activity of a nerve encompassed by an µcPNI according to an embodiment of the present invention. In particular, the upper portion of FIG. 12(a) illustrates a representative example of a chronic TSN recording aligned to the song, and the lower portions illustrate a spectrogram of the bird's song with the color indicating a power intensity at each time-frequency bin. Electrophysiology activity was recorded from the TSN simultaneously with the song motif shown with a timescale aligned shown in FIG. 12(b) The color indicates the recording channel.

In more detail, FIG. 12(b) illustrates a mean song-aligned TSN activity envelope over n=10 consecutive motifs for each channel using the same animal as shown in FIG. 12(a). Further, FIG. 12(c) illustrates a matrix of pair-wise correlations between mean song-aligned activity envelopes from each channel (n=50 each channel; 300 total) for the representative animal shown in FIG. 12(a). The row and column relations to the channel indicated by the colored lines at left and bottom.

FIG. 12(d) illustrates a mean pair-wise correlation between nerve activity envelopes recorded within (left) and across (right) µcPNI electrode in n=3 birds. The data points show the mean across electrodes within a bird, the bars show mean across all birds, and the error bars indicate std. **P<0.01 two-tailed paired t-test, P=0.008. Further, FIG. 12(e) include graphs with metrics demonstrating stable performance of each µcPNI channel over time. In particular, the left graph in FIG. 12(e) illustrates the mean daily trial-by-trial Pearson's correlation to the average activity pattern on the 1st day of recording, the center graph illustrates the mean daily peak-to-peak voltage and the right graph illustrates the mean daily event rate. In addition, FIG. 12(f) is similar to FIG. 12(e), but further illustrates the mean statistics across all electrode channels in n=3 birds (two-tailed paired t-test; correlation: P>0.17; Vpp: P>0.68; event rate: P>0.37).

The acute studies probe the PNS physiology, and provide a brief snapshot of nerve function. However, the nerve function is modulated in other contexts or by slower developmental, disease, or restorative processes. Thus, to further confirm the advantageous performance of the µcPNI for chronic recordings from a small nerve, the µcPNI as implanted on the songbirds TSN, the primary output of the singing-related central neural circuits and the sole source of innervation to the syrinx. The singing-related nerve activity was then recorded from tethered freely moving birds (n=3; FIG. 12).

All animals showed normal behavior with usual food intake, unencumbered movement, and resumption of spontaneous singing within two days of the implant. There were no signs of pain, distress, or other impairment due to the presence of the implanted µcPNI. From the first utterances, robust singing-related multi-unit activity was observed with amplitude modulations of up to 200 µV on all six electrode channels. These signals survived common-mode subtraction and filtering (FIG. 12(a)), supporting their neuronal (vs artifactual or electromyographic) origin. Consistent with prior studies of song-related neuronal activity, stereotyped segments of song (the top portion of FIG. 12(a)) were reliably associated with signal envelopes exhibiting similar time-varying trajectories.

Furthermore, daily mean signal envelopes were broadly correlated across channels with these signal envelopes also showing small but reliable deviations at discrete time points (FIG. 12(b)). To quantify these similarities, the Pearson correlation was calculated between song-aligned activity envelopes from each channel (n=500 trials across six channels in one bird, and 3000 signal envelopes in total) (FIG. 12(c)). Across experiments, signal envelopes recorded on the same electrode were significantly more correlated than those recorded on adjacent electrodes (n=3 birds, P=0.008; FIG. 12(d)). This finding echoes a similar observation in the acute experiments (FIG. 11(e)) and further illustrates that the spatially distributed electrodes are sampling unique subcomponents of TSN activity. Singing-related TSN activity in unrestrained zebra finches was recorded for up to 24 days (n=3 birds, range: 14-24 days).

Over the duration of the experiments, the recordings illustrated well-defined signals on each channel and a significant degree of stereotypy in song-aligned activity envelopes. To quantify the stability of these recordings over time, trial-by-trial for each channel, the Pearson correlation was calculated between song-aligned TSN activity envelopes and the mean envelope on day 1 (left portion of FIG. 12(e)), the Vpp of singing-related activity (center portion of FIG. 12(e)), and the mean spike event rate (right portion of FIG. 12(e)). Across n=3 birds, no significant differences were determined in the daily means of these metrics across channels between day 1 and the last day of recording (correlation: P>0.17; Vpp: P>0.68; event rate: P>0.37; FIG. 12(f)). The above experiment indicating stable longitudinal recordings of TSN activity further illustrates that the μcPNI is advantages for recording the PNS function at chronic timescales.

Figure 13:
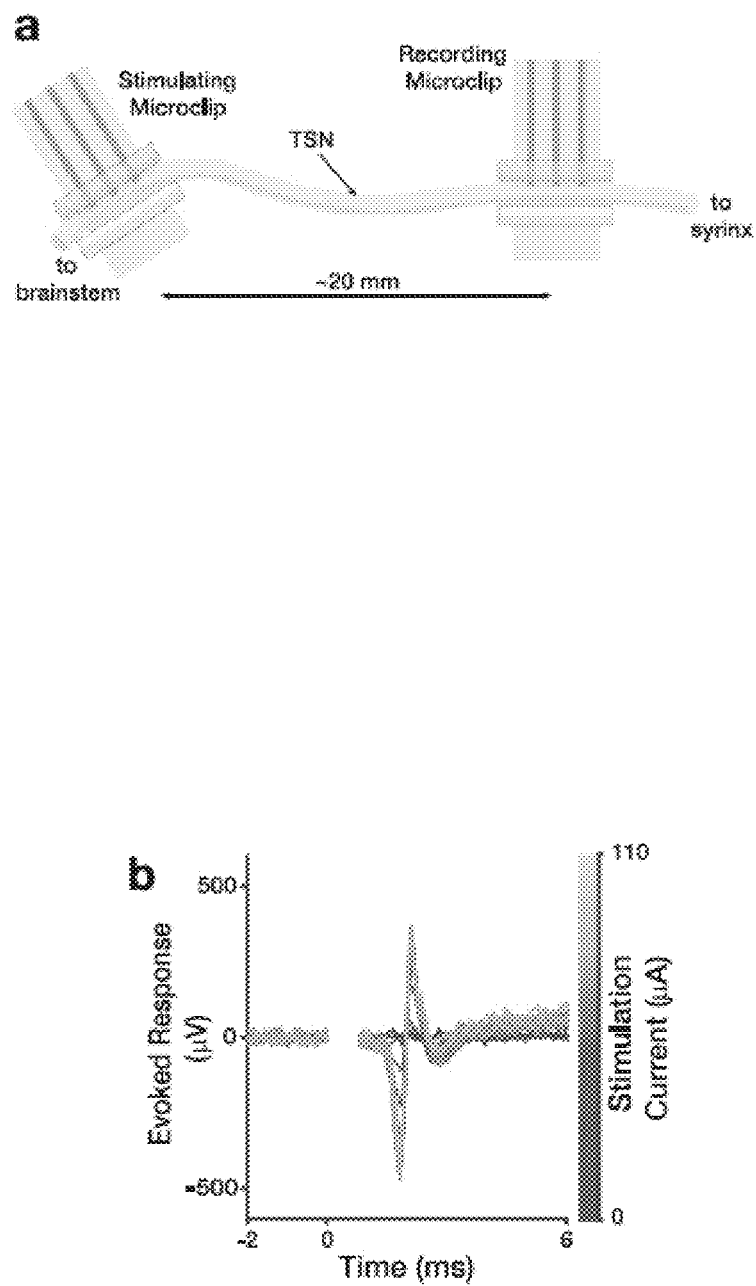
FIG. 13 includes an overview illustrating acute stimulation and recording of a TSN using multiple microclips and graphs illustrating corresponding results of the acute stimulation according to an embodiment of the present invention.
Figure 13:
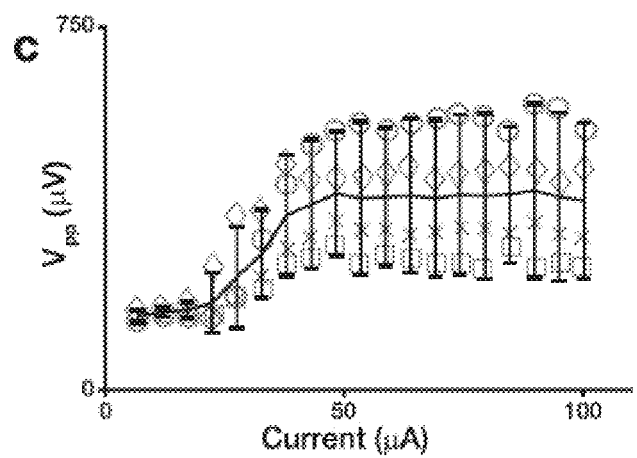
Figure 13:
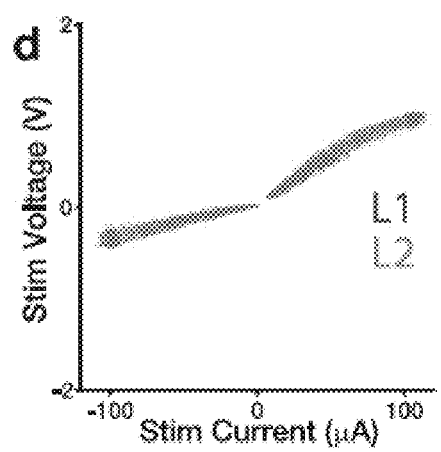

FIG. 13 includes an overview illustrating a schema for acute stimulation of a TSN and graphs illustrating corresponding results of the acute stimulation according to an embodiment of the present invention. In particular, FIG. 13(a) is a schema for acute stimulation of evoked responses in which current-controlled stimulation was delivered via a μcPNI, and evoked responses were recorded by an additional μcPNI placed approximately 20 mm caudally. FIG. 13(b) is a graph illustrating representative examples of responses evoked by graded stimulation currents with stimulation of 10-110 μA of biphasic pulses and 200 μs phase$^{-1}$ applied at t=0 ms. Each line shows a mean response across trials (8-40 trials) at binned stimulation currents (bin width=5 μA). Further, the line color indicates a stimulation current as indicated in the color bar.

In addition, FIG. 13(c) is a graph illustrating an evoked response peak-to-peak voltage (Vpp) as a function of stimulation intensity with each data point indicating the mean across trials within an animal (8-40 trials each). The gray symbols identify individual birds, and the black lines and error bars indicate the mean and standard deviation across animals (n=4 birds). FIG. 13(d) is a summary graph illustrating stimulation voltage as a function of stimulation current across experiments (i.e., 11774 trials across experiments using n=4 μcPNI). Pulses delivered by layers L1 and L2 electrode pads are indicated by color.

Further, to determine the acute stimulating performance in vivo, a two-interface preparation was used to record responses with one μcPNI that were evoked via the second μcPNI placed approximately 20 mm caudally (FIG. 13(a)). The biphasic, current-controlled stimulation pulses (200 μs phase−1) were delivered at 1 Hz via two electrode sites (e.g., 1 most-caudal and 1 most-rostral electrode) at the caudally implanted μcPNI, and response voltages were recorded at the rostral μcPNI. Graded evoked responses were obtained by varying the stimulation current (FIG. 13(b)).

The Vpp of the responses showed the canonical sigmoidal relationship with stimulation current (n=4 μcPNI in FIG. 13(c)). The recruitment curve also plateaued at approximately 50 μA, which is less than half the stimulating intensity at which the bipolar hook electrode evoked responses similarly saturated (FIG. 11(d)). This lower saturation limit is evidence that the enhanced electrical isolation of the μcPNI stimulation sites provides more efficient depolarization of the tissue compared to the exposed hook electrodes. In addition, to rule out that the μcPNI electrodes were unable to deliver the commanded charge injection, the magnitude of stimulation were verified by monitoring the command current and voltage delivered by the stimulator to the electrode pad at each phase of the pulse (FIG. 13(d)).

This analysis revealed that over the range of command currents (−100 to 100 μA; n=11774 pulses), the stimulating voltage remained well below the stimulator maximum (10V) and showed no discontinuities, indicating an electrochemical limit had not been reached. In addition, the maximum evoked response in the stimulus-response curve for μcPNI (FIG. 13(c)) and hook stimulating electrodes (FIG. 11(d)) is of comparable magnitude, indicating that all fibers are stimulated with half the current in the μcPNI compared to hook electrodes. Furthermore, no significant difference was found in the current-voltage relationship for stimulating pulses mediated by electrodes on L1 of the μcPNI versus those on L2 (P=0.53). Thus, the μcPNI is also advantageous for full-duplex acute interfacing with small peripheral nerves.

As described above, the μcPNI according to embodiments of the present invention are advantageous for several reasons. For example, the μcPNI is a microscale nerve interface that combines a soft, stretchable electrode array with a 3D-printed nerve anchor (microclip). The μcPNI provides a stable bioelectronic interface under deformation and mechanical strain comparable to those inflicted on implants by body movement. In addition, the μcPNI can record stable, high quality recordings of a small nerve in a tethered freely moving animal over multi-week timescales. Finally, the μcPNI can also achieve graded neuromodulation of a small nerve.

The ability to capture robust signals in chronic experiments highlights the advantages of the stretchable, low impedance interface according to embodiments of the present invention. There are many advantages of the μcPNI compared to related art PNI formats. For example, the compact design and the possibility to easily adapt the shape facilitate the surgical procedure alleviating the need to position and suture individual microwires. In addition, the stretchable properties of the electrode and its interconnect allow for long-term recordings. Like many peripheral nerves, the TSN runs along the trachea distant from any rigid support tissue and during animal movement the area is subjected to significant motion and displacements. In related art PNIs made from rigid bulky materials, body dynamics are related to device failure in chronic conditions occurring a few days after surgery. On the contrary, the stretchable electrode and microclip according to the present invention can adapt to the dynamic environment without generating interfacial forces that potentially damage or displace the device.

Although the description above describes an implantable device for bioelectronic interfacing for small nerves, the materials, microclip design concept, and microfabrication techniques of the μcPNI can also be used for other soft medical electronics. Securely placing implantable sensors on or nearby the soft, delicate tissues of the body is a major scientific and engineering challenge, for example, in the study of the vasculature, secretory organs, and ducts, or other active tissues. The above description thus impacts biomedical research and tool development broadly.

Further, the in vivo electrophysiology described above were controlled using custom LabVIEW (National Instruments) and MATLAB (MathWorks) software applications. Acute electrophysiological data were recorded on the right-side TSN using μcPNI interfaces with an RZ5 BioAmp Processor and an RA16PA Medusa Preamplifier (Tucker-Davis Technologies). Neural signals were digitized at 24.4 kHz and 16-bit depth and were Bessel bandpass filtered (1 Hz to 10 kHz, zero-phase). Stimulation currents were delivered through either bipolar silver hook electrodes or a second μcPNI using a PlexStim programmable stimulator (Plexon).

In addition, the current pulses were biphasic, 200 μs phase$^{-1}$ in duration, delivered at 1 Hz, and varied in amplitudes from −110 to 110 μA. The positive current amplitudes were cathodic, and the negative current amplitudes were anodic. For chronic experiments, the songbirds were recorded continuously using sound-triggered software, generating a complete record of vocalizations and nerve activity for the experiment. In addition, neural recordings were acquired with an RHD 2000 system with a 16-channel unipolar input headstage (Intan Technologies), amplified, and bandpass filtered (0.3-15 kHz). Singing-related nerve activity was recorded from six sites on the TSN in n=3 birds.

The electrophysiology data analysis was performed offline using MATLAB. In more detail, activity approximately 5 ms before and up to 25 ms after stimulation onset were sampled and used the onset of the stimulation artifact (FIGS. 11(b) and 13(b) at 0 ms) to temporally align individual trial responses. Absolute response amplitudes were observed and quantified in a stimulation response window 0.75-4 ms after stimulation onset—a latency consistent with estimated nerve conduction velocities for 4-6 μm diameter myelinated axons (i.e., 4-24 m s$^{-1}$). An evoked response was considered to be detected if the SNR within the signal response window exceeded a 90% confidence interval calculated by bootstrap (i.e., resampling with replacement of the signal and noise intervals over n=10000 trials).

As described above, FIGS. 11(b) and 13(b) show individual stimulation trials from single experimental sessions. The lines in FIGS. 11(c) and 11(e) illustrate mean responses over n=16-64 trials in an exemplary bird. Data points in FIGS. 11(d) and 13(c) illustrate a mean response at each stimulation intensity over n=64 trials for each bird; symbols identify individual birds. Further, FIG. 11(f) illustrate the mean (solid line) and standard error (shaded region) across trials, and FIG. 11(g) illustrates the mean (bar) and standard deviation (error bars) across animals; symbols identify individual animals.

Further, raw audio recordings were segmented into syllables as previously described. Briefly, spectrograms were calculated for all prospective syllables, and a neural network (5000 input layer, 100 hidden layers, 3-10 output layer neurons) was trained to identify syllable types using a manually created test data set by visual inspection of song spectrograms. Accuracy of the automated annotation was verified by visual inspection of a subset of syllable spectrograms.

Further, a dynamic time warping algorithm was used to align individual song motifs to a common template as previously described. The warping path derived from this alignment was then applied to the corresponding common mode subtracted and bandpass filtered TSN voltage recordings (0.3-6 kHz, zero-phase, 2-pole Butterworth) with no premotor time-shifting. The aligned neural traces were squared (to calculate signal envelope) and smoothed (20 ms boxcar window, 1 ms advance).

The stability of recorded TSN temporal dynamics was calculated as the Pearson's correlation between the aligned neural signal envelope (averaged over 25 consecutive motifs) on the first day of recording with the same at later time points. The day 1 data point in FIGS. 12(e) and (f) denotes the correlation between the mean signal envelopes for two consecutive blocks of 25 motifs recorded on the first day. The running correlation (FIGS. 12(e) and (f)) shows Pearson's correlation between the mean activity envelope of 25 motifs on the first day of recording and the mean of signal envelopes in a sliding window (width: 25; advance: 1).

Further, the trial-by-trial peak-to-peak voltage of singing-related nerve activity was calculated as the difference of the maximum and minimum voltage recorded for each song motif. The data points in FIGS. 12(e) and (f) denote the mean peak-to-peak voltage over all trials produced in a day.

In addition, the trial-by-trial event rate of singing related nerve activity was calculated as the number of envelope threshold crossings per unit time. A unique threshold was calculated for each motif at 5 standard deviations over the mean during singing; duration of the unwarped song was used to calculate rates. The data points in FIGS. 12(e) and (f) denote the mean event rate over all trials produced in a day.

Further, the statistics on data pooled across animals were described as mean±SD and depicted in figure error bars as mean±SD, unless otherwise noted. Figure starring schema: *P<0.05, P<0.01, and *P<0.001. N.S.: not significant. Where appropriate, distributions passed tests for normality (Kolmogorov-Smirnov), equal variance (Levene), and/or sphericity (Mauchly), unless otherwise noted. Multiple comparison corrected tests were used where justified.

In addition, statistical tests for specific experiments were performed as described above and further summarized as follows. FIG. 9(d) illustrates a comparison of noise RMS on L1 and L2 (n=3 electrodes per layer). A Wilcoxon rank-sum test showed no significant differences between RMS noise measured in L1 and L2 electrodes before (P=0.4) and after (P=0.7) electroplating with platinum black.

FIG. 10(b) illustrates impedance as a function of bending radius for n=3 electrodes on each layer. A one-way ANOVA revealed no significant differences between groups (layers) at any bend radius (F=0.45, P=0.51). FIG. 10(d) illustrates an impedance as a function of bending cycle for n=3 electrodes on each layer. A one-way ANOVA revealed no significant differences between groups (layers) at any cycle number (F=3.68, P=0.078).

Also, FIG. 10(f) illustrates an impedance as a function of bending cycle for n=2 electrodes on each layer. A one-way ANOVA revealed no significant differences between groups (layers) at any cycle number (F=3.26, P=0.074). FIG. 11(g): Comparison of stimulation evoked response amplitudes before and after lidocaine/saline application in n=4 birds. A repeated measures ANOVA revealed significant differences between the treatments (F=12.65, P=0.007). Post-hoc comparisons using Dunnett's test showed significant differences in Vpp between saline (control) and lidocaine application (P=0.009); following washout, the Vpp was not significantly different from control (P=0.29).

FIG. 12(d): Comparison of mean correlation between aligned signal envelopes recorded on the same electrode and different electrodes (n=500 signal envelopes from each of 6 electrodes in n=3 birds). A two sided, paired t-test revealed that the correlation of envelops recorded on the same electrodes was significantly different (P=0.008) from those recorded on different channels. FIG. 12(f): Comparison of chronic stability metrics on the first and last day of recording in n=3 birds. For each bird, a two-tailed paired t-test showed no significant differences between the 6-channel daily mean correlations (P>0.17), mean peak-to-peak voltages (P>0.68), and event rates (P>0.37) on day 1 and those on the last day.

Various embodiments described herein may be implemented in a computer-readable medium using, for example, software, hardware, or some combination thereof. For a hardware implementation, the embodiments described herein may be implemented within one or more of Application Specific Integrated Circuits (ASICs), Digital Signal Processors (DSPs), Digital Signal Processing Devices (DSPDs), Programmable Logic Devices (PLDs), Field Programmable Gate Arrays (FPGAs), processors, controllers, micro-controllers, microprocessors, other electronic units designed to perform the functions described herein, or a selective combination thereof. In some cases, such embodiments are implemented by the controller 180. That is, the controller is a hardware-embedded processor executing the appropriate algorithms (e.g., flowcharts) for performing the described functions and thus has sufficient structure.

For a software implementation, the embodiments such as procedures and functions may be implemented together with separate software modules each of which performs at least one of functions and operations. The software codes can be implemented with a software application written in any suitable programming language. Also, the software codes may be stored in the memory and executed by the controller. Thus, the components shown in the drawings have sufficient structure to implement the appropriate algorithms for performing the described functions.

The present invention encompasses various modifications to each of the examples and embodiments discussed herein. According to the invention, one or more features described above in one embodiment or example can be equally applied to another embodiment or example described above. The features of one or more embodiments or examples described above can be combined into each of the embodiments or examples described above. Any full or partial combination of one or more embodiment or examples of the invention is also part of the invention.

As the present invention may be embodied in several forms without departing from the spirit or essential characteristics thereof, it should also be understood that the above-described embodiments are not limited by any of the details of the foregoing description, unless otherwise specified, but rather should be construed broadly within its spirit and scope as defined in the appended claims, and therefore all changes and modifications that fall within the metes and bounds of the claims, or equivalence of such metes and bounds are therefore intended to be embraced by the appended claims.

What is claimed is:

1. A peripheral nerve interface, comprising
   a microclip having a substantial U-shape and including an upper entry portion configured for entry of a nerve into the microclip and a lower seating portion configured for seating the nerve in the lower seating portion of the microclip;
   a stretchable microelectrode array including a plurality of electrodes, wherein the stretchable microelectrode array has a proximal end portion fixed to the microclip and a portion that is moveable and dragged into the upper entry portion and then the lower seating portion of the microclip in response to the microclip being positioned on the nerve; and
   an interface connected to a distal end of the stretchable microelectrode array and configured to interface with an external device for applying electrical stimulation to the nerve seated in the lower seating portion and for recording electrical characteristic of the nerve seated in the lower seating portion via the plurality of electrodes in the stretchable microelectrode array,
   wherein the microclip further comprises:
   flexion cut-out portions formed on each side of the lower seating portion; and
   pinch protrusions protruding inward and partially separating the upper entry portion and the lower seating portion,
   wherein a gap exists between the pinch protrusions that is smaller than a diameter of the nerve, and
   wherein the flexion cut-out portions compress and open the microclip for entry of the nerve into the upper entry portion and for entry of the nerve from the upper entry portion into the lower seating portion.

2. The peripheral nerve interface of claim 1, wherein the flexion cut-out portions are formed on each side of the lower seating portion at a position corresponding to a bottom surface of the lower seating portion.

3. The peripheral nerve interface of claim 1, wherein as the nerve is seated in the lower seating portion, the flexion cut-out portions un-compress and the pinch protrusions move towards each other to rest against the stretchable microelectrode array.

4. The peripheral nerve interface of claim 1, wherein the microclip comprises a 3D printed microclip.

5. The peripheral nerve interface of claim 1, wherein the microclip further comprises:
   a lower base portion;
   a first upper leg portion extending from the lower base portion; and
   a second upper leg portion extending from the lower base portion and spaced apart a predetermined distance from the first upper leg portion to form the U-shape.

6. The peripheral nerve interface of claim 5, wherein the predetermined distance between the first upper leg portion and the second upper leg portion is substantially equal to a sum of a diameter of the nerve and twice a thickness of the stretchable microelectrode array.

7. The peripheral nerve interface of claim 5, wherein each of the first upper leg portion and the second upper leg portion includes an opening for passing the stretchable microelectrode array through the first and second upper leg portions of the microclip.

8. The peripheral nerve interface of claim 1, wherein the stretchable microelectrode array comprises:
   an elastomeric substrate, and
   wherein the plurality of electrodes are formed in a single layer or different layers of the elastomeric substrate.

9. The peripheral nerve interface of claim 1, wherein the plurality of electrodes comprises microcracked gold electrodes.

10. The peripheral nerve interface of claim 1, wherein the plurality of electrodes include a first set of electrodes used for electrical stimulating the nerve and a second set of electrodes used for recording neural responses of the nerve in response to the electrical stimulation of the nerve by the first set of electrodes.

11. The peripheral nerve interface of claim 1, wherein when the nerve is seated in the lower seating portion, electrode pads of the plurality of electrodes wrap around a circumference of the nerve and stimulation of the nerve is applied for modulation of neural activity and discrete signals are recorded across the circumference of the nerve via the plurality of electrodes.

12. The peripheral nerve interface of claim 1, wherein the lower seating portion comprises a circular shape.

13. A peripheral nerve interface, comprising
   a microclip having a substantial U-shape and including an upper entry portion configured for entry of a nerve into the microclip and a lower seating portion configured for seating the nerve in the lower seating portion of the microclip;
   a stretchable microelectrode array including a plurality of electrodes, wherein the stretchable microelectrode array has a proximal end portion fixed to the microclip and a portion that is moveable and dragged into the upper entry portion and then the lower seating portion of the microclip in response to the microclip being positioned on the nerve; and an interface connected to a distal end of the stretchable microelectrode array and configured to interface with an external device for applying electrical stimulation to the nerve seated in the lower seating portion and for recording electrical characteristic of the nerve seated in the lower seating portion via the plurality of electrodes in the stretchable microelectrode array, wherein the microclip further comprises:

a manipulation hole for receiving a pin tool, and wherein the microclip is moved forward against the nerve by surgical manipulation of the pin tool inserted into the manipulation hole.

14. A peripheral nerve interface, comprising a microclip having a substantial U-shape and including an upper entry portion configured for entry of a nerve into the microclip and a lower seating portion configured for seating the nerve in the lower seating portion of the microclip;

a stretchable microelectrode array including a plurality of electrodes, wherein the stretchable microelectrode array has a proximal end portion fixed to the microclip and a portion that is moveable and dragged into the upper entry portion and then the lower seating portion of the microclip in response to the microclip being positioned on the nerve; and an interface connected to a distal end of the stretchable microelectrode array and configured to interface with an external device for applying electrical stimulation to the nerve seated in the lower seating portion and for recording electrical characteristic of the nerve seated in the lower seating portion via the plurality of electrodes in the stretchable microelectrode array, wherein the microclip further comprises:

a lower base portion;

a first upper leg portion extending from the lower base portion; and a second upper leg portion extending from the lower base portion and spaced apart a predetermined distance from the first upper leg portion to form the U-shape, wherein each of the first upper leg portion and the second upper leg portion includes an opening for passing the stretchable microelectrode array through the first and second upper leg portions of the microclip, wherein the first upper leg portion includes a first base portion and a first cap portion at the upper entry portion, wherein the second upper leg portion includes a second base portion and a second cap portion at the upper entry portion, wherein the second base portion of the second upper leg portion includes at least a first printed electrode clamp protruding towards the second cap portion, and wherein the second cap portion of the second upper leg portion includes at least a second printed electrode clamp protruding towards the second base portion to clamp the stretchable electrode array to the microclip.

15. The peripheral nerve interface of claim 14, wherein the first and second printed electrode clamps are spaced apart from one other by a distance equal to thickness of the stretchable electrode array under strain.

16. The peripheral nerve interface of claim 15, wherein upon release of the strain of the stretchable electrode array, the first and second printed electrode clamps protrude into the stretchable microelectrode array to clamp the stretchable microelectrode array to the microclip.

17. The peripheral nerve interface of claim 16, wherein the stretchable microelectrode array passes freely through on opening between the first base portion and the first cap portion of the first upper leg portion.

* * * * *